US009789195B2

(12) United States Patent
Cheng et al.

(10) Patent No.: US 9,789,195 B2
(45) Date of Patent: Oct. 17, 2017

(54) PARTICULATE DRUG DELIVERY METHODS

(71) Applicant: The Board of Trustees of the University of Illinois, Urbana, IL (US)

(72) Inventors: Jianjun Cheng, Champaign, IL (US); Rong Tong, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 14/530,174

(22) Filed: Oct. 31, 2014

(65) Prior Publication Data

US 2015/0314006 A1    Nov. 5, 2015

Related U.S. Application Data

(62) Division of application No. 12/041,529, filed on Mar. 3, 2008, now abandoned.

(60) Provisional application No. 60/892,834, filed on Mar. 2, 2007.

(51) Int. Cl.
| | |
|---|---|
| C08G 63/82 | (2006.01) |
| A61K 47/48 | (2006.01) |
| C08G 81/00 | (2006.01) |
| A61K 31/337 | (2006.01) |
| A61K 31/704 | (2006.01) |
| A61K 38/09 | (2006.01) |
| A61K 9/51 | (2006.01) |
| A61K 38/13 | (2006.01) |
| A61K 31/4355 | (2006.01) |

(52) U.S. Cl.
CPC ......... *A61K 47/482* (2013.01); *A61K 9/5146* (2013.01); *A61K 9/5192* (2013.01); *A61K 31/337* (2013.01); *A61K 31/4355* (2013.01); *A61K 31/704* (2013.01); *A61K 38/09* (2013.01); *A61K 38/13* (2013.01); *A61K 47/48215* (2013.01); *A61K 47/48407* (2013.01); *A61K 47/48584* (2013.01); *A61K 47/48669* (2013.01); *A61K 47/48876* (2013.01); *A61K 47/48907* (2013.01); *A61K 47/48915* (2013.01); *C08G 63/823* (2013.01); *C08G 81/00* (2013.01)

(58) Field of Classification Search
None
See application file for complete search history.

(56) References Cited

U.S. PATENT DOCUMENTS

| | | | |
|---|---|---|---|
| 4,523,591 A | 6/1985 | Kaplan et al. | |
| 5,981,743 A | 11/1999 | Gross et al. | |
| 6,007,845 A | 12/1999 | Domb et al. | |
| 6,245,349 B1 | 6/2001 | Yiv et al. | |
| 6,316,590 B1 | 11/2001 | Coates et al. | |
| 6,365,173 B1 | 4/2002 | Domb et al. | |
| 6,506,405 B1 | 1/2003 | Desai et al. | |
| 6,589,548 B1 | 7/2003 | Oh et al. | |
| 6,753,006 B1 | 6/2004 | Desai et al. | |
| 7,163,697 B2 | 1/2007 | Hanes et al. | |
| 2003/0185895 A1 | 10/2003 | Lanphere et al. | |
| 2004/0253601 A1 | 12/2004 | Moon et al. | |
| 2005/0058603 A1 | 3/2005 | Gao et al. | |
| 2005/0176661 A1 | 8/2005 | Vaillant et al. | |
| 2005/0276841 A1 | 12/2005 | Davis et al. | |
| 2006/0073209 A1 | 4/2006 | Sung et al. | |
| 2006/0182778 A1 | 8/2006 | Balar et al. | |
| 2007/0071790 A1 | 3/2007 | Ameer et al. | |

FOREIGN PATENT DOCUMENTS

WO    2005092097 A1    10/2005

OTHER PUBLICATIONS

Illum, L. et al, FEBS Letters, vol. 167, No. 1 (Feb. 1984), pp. 79-82.*
Veld, Peter J. A. In'T, et al., Journal of Polymer Science: Part A: Polymer Chemistry, vol. 35, (1997), pp. 219-226.*
Marbef, Dichloromethane, (accessed Oct. 18, 2016, p. 1.*
Song et al., Chinese Chemical Letters, 2003. 14: pp. 32-34.
Andrianov et al., "Protein Release from Polyphosphazene Matrices," Adv. Drug Deliv., Rev. 31, 1998, pp. 185-196.
Avgoustakis et al. (2002) "PLGA-mPEG Nanoparticles of Cisplatin: in Vitro Nanoparticle Degradation, in vitro Drug and in Vivo Drug Release Residence in Blood Properties," J Controlled Release 79 pp. 123-135.
Bertin et al. "High-Density Doxorubicin-Conjugated Polymeric Nanoparticles via Ring-Opening Metathesis Polymerization, " Chem. Commun., 2005 pp. 3793-3794.
Caliceti et al. "Pharmacokinetic and Biodistribution Properies of Poly(ethylene glycol)-Protein Conjugates" Adv. Drug Deliv. Rev. Sep. 2003, 55:10 pp. 1261-1277.
Carrot et al. "Novel Initiators for Atom Transfer Radical and Ring-Opening Polymerization: A New General Method for the Preparation of Thiol-Functional Polymers," Macromolecules 1999, 32: 5171-5173.

(Continued)

*Primary Examiner* — Dennis J Parad
*Assistant Examiner* — Lyndsey Beckhardt
(74) *Attorney, Agent, or Firm* — Haukaas Fortius PLLC; Michael H. Haukaas

(57) ABSTRACT

Methods for efficient preparation of drug-polymer (or oligomer) conjugates useful in the preparation of particles, including microparticles and nanoparticles, for delivery of the drug in vivo for therapeutic applications are provided. The invention also provides nanoparticles prepared by nanoprecipitation using drug-polymer/oligomer conjugates of the invention. The drug conjugates are formed during polymerization of the polymer or oligomer in which the drug is employed as an initiator of the polymerization of the monomers which form the polymer and/or oligomer. More specifically, the drug conjugates are formed by ring-opening polymerization of cyclic monomers in the presence of an appropriate ring-opening polymerization catalyst and the initiator (the drug). The method is particularly useful for formation of polymer/oligomer conjugates with drugs and other chemical species containing one or more hydroxyl groups or thiol groups.

26 Claims, 21 Drawing Sheets

(56) References Cited

OTHER PUBLICATIONS

Chamberlain et al. "Polymerization of Lactide with Zinc and Magnesium Beta-Diminate Complexes: Stereocontrol and Mechanism," J. Am. Chem. Soc. 2001, 123: 3229-3238.
Cheng et al. "Formulation of Functionalize PLGA-PEG Nanoparticles for In Vivo Targeted Drug Delivery," Biomaterials, 2007. 28: pp. 869-876Available online Oct. 20, 2006.
Cheng et al. "Single-Site Catalysts for Ring-Opening Polymerization: Synthesis of Heterotactic poly(lactic acid) from rac-lactide," J. Am. Chem. Soc., 1999 121: pp. 11583-11584.
Dechy-Cabaret et al. "Controlled Ring-Opening Polymerization of Lactide and Glycolide," Chem. Rev., 2004. 104: pp. 6147-6176.
Dong et al. "Methoxy Poly(ethylene glycol)-oily(lactide) (MPEG-PLA) Nanoparticles for Controlled Delivery of Anticancer Drugs," Biomaterials, 2004. 25: pp. 2843-2849.
Duncan, R. "Polymer Conjugates as Anticancer Nanomedicins," Nature. Rev. Cancer., 2006 6: pp. 688-701.
Duncan. R. "The Dawning Era of Polymer Therapeutics," Nature Rev. Drug Disc., 2003 2: pp. 347-360.
Farokhzad et al. "Targeted Nanoparticle Aptamer Bioconjugates for Cancer Chemotherapy in Vivo," Pro. Nat. Acad. Sci. USA., 2006. 103: pp. 6315-6320.
Feng et al. "Nanoparticles of Biodegradable Polymers for Clinical Administration of Paclitaxel," Curr. Med. Chem., 2004. 11: pp. 413-424.
Gao et al. "In Vivo Cancer Targeting and Imaging with Semiconductor Quantum Dots," Nat. Biotechnol., 2004. 22: pp. 969-976.
Gillies, E.R. et al., "Designing macromolecules for therapeutic applications: polyester dendrimer—poly(ehtylene oxide) "bow-tie" hybrids with tunable molecular weight and architecture", J. Am. Chem. Soc., vol. 124, No. 47, Aug. 11, 2002, pp. 14137-14146.
Govender et al. "PLGA Nanoparticles Prepared by Nanoprecipitation: Drug Loading Release Studies of a Water Soluable Drug," J. Controlled Release., Feb. 1999. 57(2): pp. 171-185.
Gradishar, W.J. "Albumin-Bound Paclitaxel: A Next-Generation Taxane," Exp. Opin. Pharmacotherapy., 2006. 7: pp. 1041-1053.
Gref et al. "Biodegradable Long-Circulation Polymeric Nanospheres," Science., Mar. 1994. 263: pp. 1600-1603.
Haag et al. " Polymer Therapeutics: Concepts and Applications," Angew. Chem. Int Ed., 2006. 45: pp. 1198-1215.
Hans et al. "Synthesis and Characterization of mPEG-PLA Prodrug Micelles," Biomacromolocules, 2005. 6: pp. 2708-2717.
Katoaka et al. "Block Copolymer Micelles for Drug Delivery: Design, Characterization and Biological Significance," Adv. Drug Deliv. Rev., 2001. 47: pp. 113-131.
Kim. C.J. "Effects of Drug Solubility, Drug Loading, and Polymer Molecular Weight on Drug Release from Polyox (R) Tablets," Drug Dev. Ind. Pharm., 1998. 24: 645-651.
Kwon et al. "Block-Copolymer Micelles as Long-Circulating Drug Vehicles," Adv. Drug. Deliv. Rev., 1995. 16: pp. 295-309.
Lavasanifar et al. "Poly(ethylene Oxide)-Block-poly(L-amino acid) Micelled for Drug Delivery," Adv. Drug. Deliv. Rev., 2002. 54: pp. 169-190.
Lu et al. "Hexamthyldisilacane-Mediated Controlled Polymerization of a-Amino Acid N-Carboxyanhydrides," J. Am. Chem. Soc., 2007. 129(46): pp. 14115 published online Oct. 27, 2007.
Magri et al. "Modified Taxols 3. Preparation and Acylation of Baccatin III," J. Org. Chem., 1986. 51(16) pp. 3239-3242.
Mastropaolo et al. "Crystal and Molecular Structure of Paclitaxel (taxol)," Proc., Nat. Acad. Sci., Jul. 1995. USA. 92: pp. 6920-6924.
Mathew, A.E., "Synthesis and evaluation of some water-soluble prodrugs and derivatives of taxol with antitumor activity", J. Med. Chem., vol. 35, 1992, pp. 145-151.
Moghimi et al "Nanomedicine: Current Status and Future Prospects," Faseb J., 2005. 19: pp. 311-330.
Mu, L. et al., "Study on surfactant coating of polymeric nanoparticles for controlled delivery of anticancer drug", Colloid Polym Sci (2004) 283, pp. 58-65.
Musumeci et al. "PLA/PLGA Nanoparticles for Sustained release of Docetaxel," Int. J. Pharmaceutics, 2006. 325: pp. 172-179.
Nishiyama et al. "Nanostructured Devices Based on Block Copolymer Assemblies for Drug Delivery: Designing Structures for Enhanced Drug Function," Adv. Polym. Sci., 2006. 193: pp. 67-101.
Pierri et al. "Poly-lactide)poly(ethylene glycol) Micelles as a Carrier for Griseofulvin," J. Biomed. Mater. Res. A, 2005. 75(3): pp. 639-647.
Pratt et al. "Triazabicyclodecene: A Simple Bifunctional Organocatalyst for Acyl Transfer and Ring-Opening Polymerization of Cyclic Esters," J. Am. Chem. Soc., 2006. 128: pp. 4556-4557.
Soppimath et al. "Biodegradable Polymeric Nanoparticles as Drug Delivery Devices," J. Controlled Release, 2001. 70: pp. 1-20.
Tong et al. "Pacitaxel-Initiated, Controlled Polymerization of Lactide for the Formulation of Polymeric Nanoparticulate Delivery Vehicles," Angew. Chem., 2008. 120: pp. 4908-4912.
Wagner et al. "The Emerging Nanomedicine Landscape," Nat. Biotechnol., 2006. 24: pp. 1211-1217.
Yoo et al., "Biodegradable Nanoparticles Containing Doxorubicin-PLGA Conjugate for Sustained Release," Pharmaceutical Research, Nov. 7, 1999. 16: pp. 1114-1118.
Yoo et al., "In vitro and in vivo anti-tumor activities of nanoparticles based on doxorubicin-PLGA conjugates," Journal of Controlled Release, May 18, 2000. pp. 419-431.
International Search Report and Written Opinion for PCT/US08155590 dated Jul. 15, 2008, 11 pp.

\* cited by examiner

♦ = (BDI)MN(TMS)$_2$ (M = Mg, Zn);   ♦-● = (BDI)M-Ptxl   ∼∼∼ = PLGA-mPEG
● = Paclitaxel (Ptxl)   ○ = Lactide (LA)   ∼∼∼● = (BDI)M-Ptxl-LA$_n$ Fig. 10A
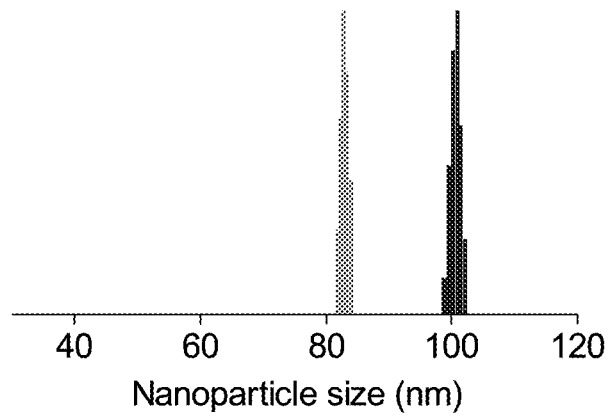
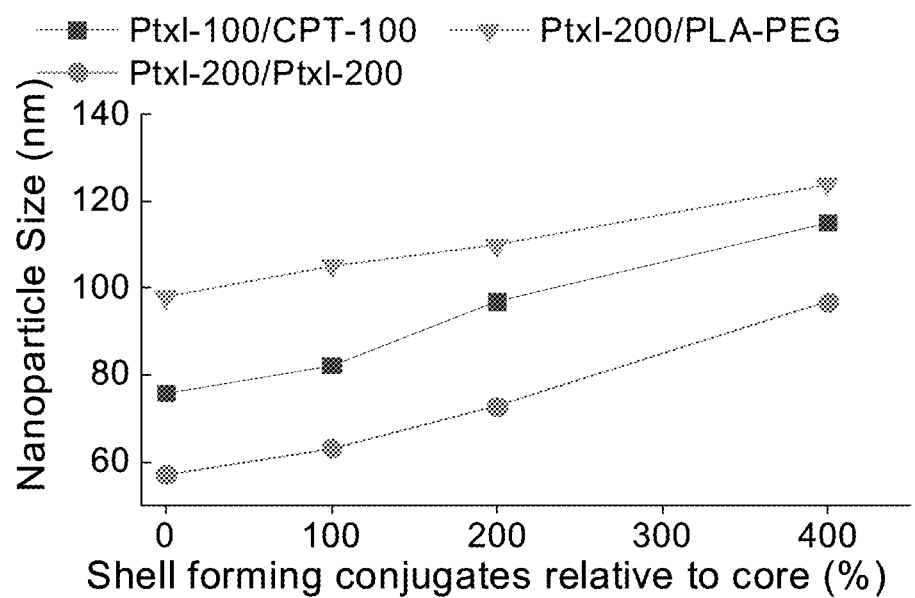
Fig. 10B

DRUGS CONTAINING OH GROUPS USEFUL FOR POLYMER DRUG CONJUGATES

| Drug Name | Mechanism | Disease treated | Hydroxyl groups available for oligomer/polymer binding | Structure |
|---|---|---|---|---|
| Anti-Cancer | | | | |
| Doxorubicin<br><br>Other anthracycline family: (Daunorubicin, Epirubicin, Idarubicin, Mitoxantrone, Valrubicin, Bleomycin) | binding to DNA where it can inhibit the progression of the enzyme topoisomerase II, which unwinds DNA for transcription | treat Hodgkin's disease, breast cancer, lung cancer, soft tissue sarcoma, Kahler's disease (multiple myeloma) and recurring instances of ovarian cancer. | 3 (1-1' OH; 1-2 OH, and 1-3' OH) | 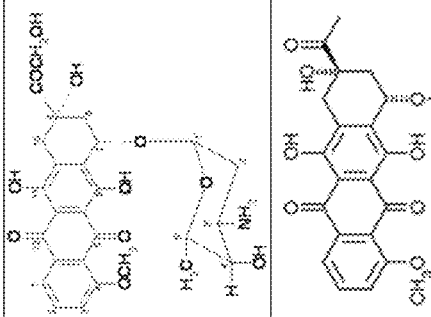 |
| Daunorubicin | | | 2 OH (1-2' OH, and 1-3' OH) | 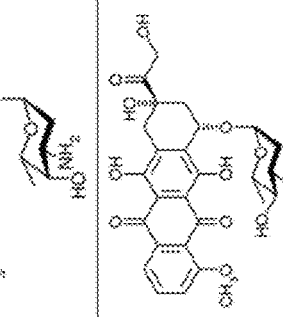 |
| Epirubicin | | | 3 OH (1-1' OH, 1-2' OH, and 1-3' OH) | 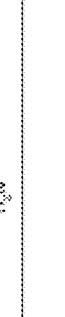 |

Fig. 13

| Drug Name | Mechanism | Disease treated | Hydroxyl groups available for oligomer/polymer binding | Structure |
|---|---|---|---|---|
| Mitoxantrone | | Also used to treat certain forms of MS | 2 OH (2-1' OH) | 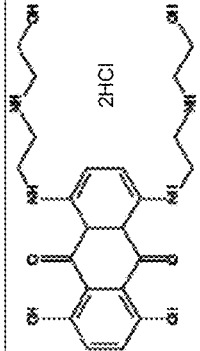 |
| Bleomycins | | | 8 OH (2-1' OH and 6-2' OH) | 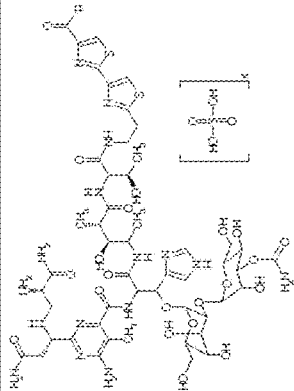 |
| Cinca alkaloids | | | | |
| Vincristine | Vincristine binds to tubulin dimers causing disassembly of microtubule structures | non Hodgkin's lymphoma, Hodgkin's lymphoma, acute lymphoblastic leukemia | 2(2"OH) | 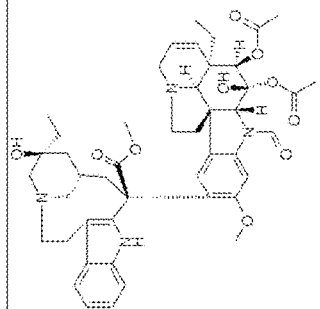 |

Fig. 13 (cont.)

| Drug Name | Mechanism | Disease treated | Hydroxyl groups available for oligomer/polymer binding | Structure |
|---|---|---|---|---|
| Vinblastine | binds tubulin, thereby inhibiting the assembly of microtubules | ABVD for Hodgkin lymphoma | 2(2"OH) | 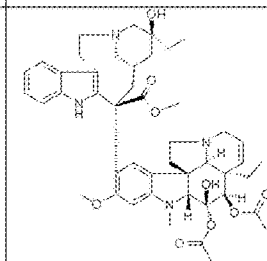 |
| Vinorelbine | | | 1 OH (1-3' OH) | 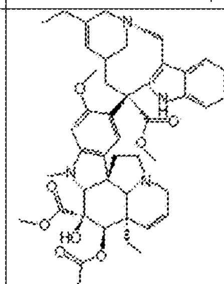 |
| Vindesine | | | 3(2"OH) | 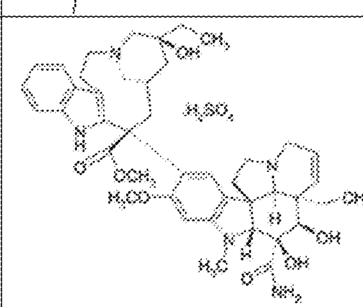 |

| Drug Name | Mechanism | Disease treated | Hydroxyl groups available for oligomer/polymer binding | Structure |
|---|---|---|---|---|
| Non-alkaloid toxin | | | | |
| Podophyllotoxin | | pharmacological base for the important anti-cancer drug Etoposide | 1 OH (2"OH) | 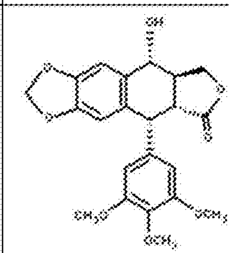 |
| Etoposide | an inhibitor of the enzyme topoisomerase II. | lung cancer, testicular cancer, lymphoma, non-lymphocytic leukemia, and glioblastoma multiforme. | 2 OH (2"OH) | 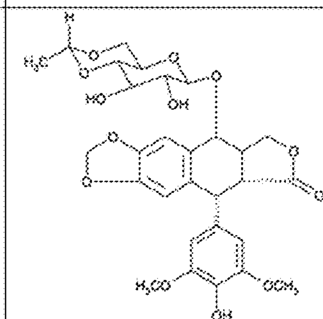 |
| Teniposide (Vumon®, VM-26) | podophyllotoxin derivatives and slows the growth of cancer cells | childhood acute lymphocytic leukemia | 2 OH (2'OH) | 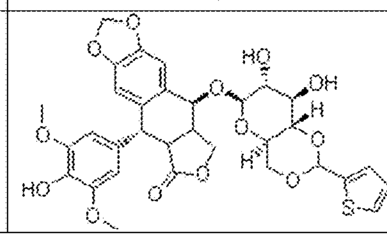 |

Fig. 13 (cont.)

| Drug Name | Mechanism | Disease treated | Hydroxyl groups available for oligomer/polymer binding | Structure |
|---|---|---|---|---|
| Taxanes (L01CD) | The principal mechanism of the taxane class of drugs is the inhibition of the microtubule function. It does this by stabilizing GDP-bound tubulin in the microtubule | | | |
| Paclitaxel | Paclitaxel interferes with the normal function of microtubule growt | lung, ovarian, breast cancer, and advanced forms of Kaposi's sarcoma | 3 (2'OH) | 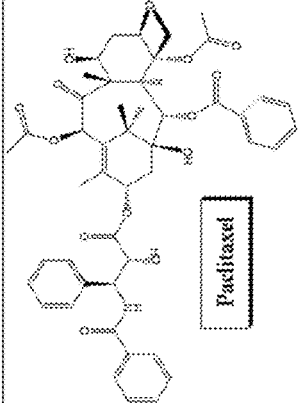 Paclitaxel |
| Docetaxel | Paclitaxel interferes with the normal function of microtubule growt | breast, prostate and other non-small cell cancers | 3 (2'OH) | 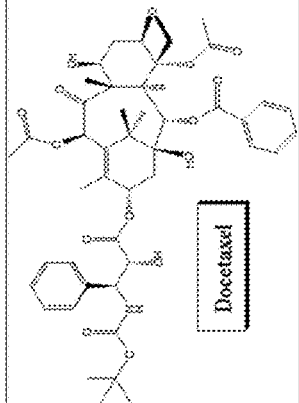 Docetaxel |

Fig. 13 (cont.)

| Drug Name | Mechanism | Disease treated | Hydroxyl groups available for oligomer/polymer binding | Structure |
|---|---|---|---|---|
| Irinotecan | a topoisomerase 1 inhibitor | colon cancer, | 1(2'OH) | 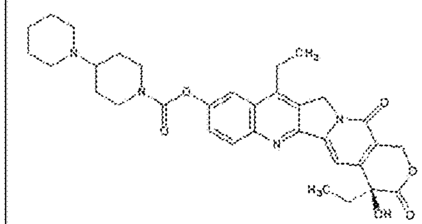 |
| Topotecan (Hycamtin®) | topoisomerase 1 inhibitor | ovarian cancer and lung cancer | 1 OH (3'OH) | 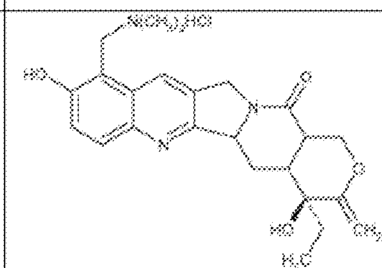 |
| Anti-viral | | | | |
| Abacavir | reverse transcriptase inhibitor (NARTI) | used to treat HIV and AIDS. | 1 OH (1'OH) | 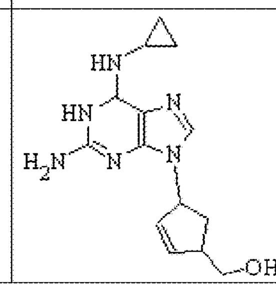 |

| Drug Name | Mechanism | Disease treated | Hydroxyl groups available for oligomer/polymer binding | Structure |
|---|---|---|---|---|
| Aciclovir | Forming Aciclo-GTP, a very potent inhibitor of viral DNA polymerase | HSV and VZV infections | 1OH (1'OH) | 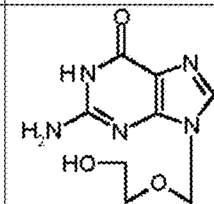 |
| Didanosine | reverse transcriptase inhibitor; it is phosphorylated to the active metabolite of dideoxyadenosine triphosphate, ddATP, by cellular enzymes, it acts as a chain terminator by incorporation and inhibits viral reverse transcriptase by competing with natural dATP | HIV | 1 OH (1'OH) | 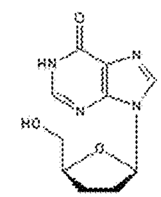 |
| Darunavir | a protease inhibitor | HIV | 1 OH (2' OH) | 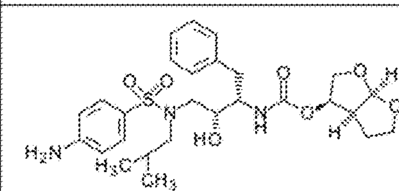 |

Fig. 13 (cont.)

| Drug Name | Mechanism | Disease treated | Hydroxyl groups available for oligomer/polymer binding | Structure |
|---|---|---|---|---|
| Ribavirin | Ribavirin 5'-monophosphate inhibits cellular inosine monophosphate dehydrogenase, thereby depleting intracellular pools of GTP. | influenzas, flaviviruses viral hemorrhagic fevers | 3 (one 1' OH; two 2' OH) | 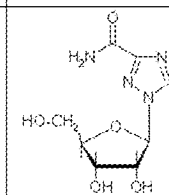 |
| Anti-fungal | | | | |
| Natamycin | | fungal keratitis, especially effective against *Aspergillus* and *Fusarium* corneal infections | 5 (all 2'OH) | 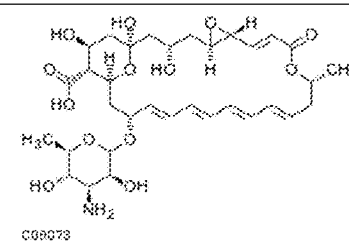 |
| Fluconazole | inhibits the fungal cytochrome P450 enzyme 14α-demethylase. This inhibition prevents the conversion of lanosterol to ergosterol, an essential component of the fungal cytoplasmic membrane, and subsequent accumulation of 14α-methyl sterols | Candidiasis, Tinea corporis, tinea cruris or tinea pedis. Et.al. | 1 OH (3'-OH) | fluconazole |

Fig. 13 (cont.)

| Drug Name | Mechanism | Disease treated | Hydroxyl groups available for oligomer/polymer binding | Structure |
|---|---|---|---|---|
| Posaconazole | | invasive infections by *Candida* species and *Aspergillus* species | 1 OH (2'-OH) | 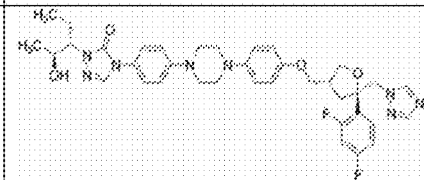 |
| Voriconazole | . | invasive fungal infections, including invasive candidiasis, invasive aspergillosis, and emerging fungal infections | 1 OH (3'-OH) | voriconazole |
| Caspofungin | | *Aspergillus* and *Candida* | 7 OH (2'-OH) | 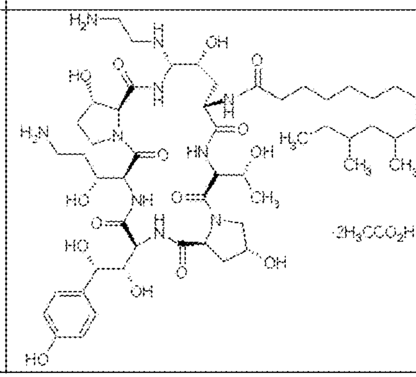 |

Fig. 13 (cont.)

| Drug Name | Mechanism | Disease treated | Hydroxyl groups available for oligomer/polymer binding | Structure |
|---|---|---|---|---|
| Amphotericin B | associates with ergosterol, a membrane chemical of fungi, forming a pore that leads to K+ leakage and fungal cell death | oral thrush, visceral leishmaniasis, Aspergillosis, cryptococcus | 10 (2'OH) | 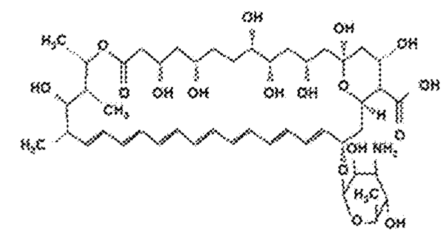 |
| Antibacterial | | | | |
| Phenoxyethanol | | used in place of sodium azide in biological buffers | 1 OH (1' OH) | 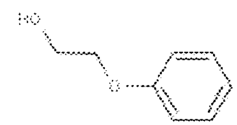 |

Fig. 13 (cont.)

PARTICULATE DRUG DELIVERY METHODS

CROSS-REFERENCE TO RELATED APPLICATIONS

This application is a divisional of U.S. patent application Ser. No. 12/041,529, filed Mar. 3, 2008, which claims priority from U.S. Provisional Application No. 60/892,834, filed Mar. 2, 2007, which applications are incorporated herein by reference.

BACKGROUND OF THE INVENTION

Polymer nanoparticles (NPs) play an important role in drug delivery and are particularly useful for delivery of chemotherapy drugs. For clinical applications, the control of nanoparticle size and surface morphology are important. Other aspects of the design of particulate systems can also be important for the use of nanoparticles as delivery systems in vivo. It is preferred that drug loading in the polymeric nanoparticle is reasonable high for improved efficacy. This is particularly important for enhanced effectiveness of nanoparticles in cancer therapy [1-3]

High drug loading[4,5] decreases manufacturing cost and increases patient compliance by reducing the dose needed for each administration. In addition, drug molecules in nanoparticle delivery vehicles preferably remain substantially encapsulated in the polymeric nanoparticles on administration to a patient to be released in a sustained manner over time or after they accumulate at a desired location. More specifically for nanoparticle applications to cancer therapy, it is important that anticancer agents remain encapsulated with little or no drug release while in the vasculature and release the anticancer agent only after the nanoparticles extravasate to tumor tissues.

Well-controlled drug release has been realized only in a limited number of drug delivery systems, most of which are liposomes.[6] Currently, there are about 10 liposomal delivery vehicles approved for clinical applications of which only one, Abraxane, an albumin bound paclitaxel nanoparticle with size ~130 nm, is a polymeric nanoparticulate delivery vehicle.[6,7] Abraxane,[8,9] appears to contain a large quantity of lipids on the surface of albumin nanoparticles which gives them liposome-like properties in regulating drug release. To date no polyester based nanoencapsulates are approved for clinical cancer treatment.

In a recent study using poly(ethylene glycol)-b-poly(lactide-co-glycolide) (PEG-PLGA) to nanoencapsulate docetaxel for in vivo prostate cancer treatment (Farokhzad, O. C.; Cheng, J.; Teply, B. A.; Sherifi, I.; Jon, S.; Kantoff, P. W.; Richie, J. P.; Langer, R. Proc. Nat'l Acad.Sci. (USA) 2006, 103, 6315-6320), difficulties were experienced in controlling formulation parameters such as drug loading and encapsulation efficiency. The encapsulation efficiency, which depends on various parameters, including solvents, type of polymers, polymer molecular weights, and the drugs to be encapsulated, varied from batch to batch and was usually less than 80%. Drug loading was also typically lower than 10%. In many cases, only 1% of drug loading could be achieved. NPs with more than 5% of drug loading sometimes contained undesired large aggregates (>1 micron), which was presumably due to the aggregation of the non-encapsulated drug molecules. Particles with mixed sizes and wide distributions can lead to complex biodistribution and pharmacokinetic responses in vivo.

In liposome delivery systems, drug molecules are encapsulated in the core of the liposome and are, thus, separated from the external environment by lipid bi-layers which prevent leakage of encapsulated drug molecules. In contrast, polymer nanoencapsulates (polymeric nanoparticles) have no such regulating mechanism to prevent the unwanted leaking of therapeutic molecules during circulation. Significant burst release effects are one of the greatest challenges to overcome in the application of polymeric nanoparticles in vivo for drug delivery. In a vehicle with significant burst release effect, poorly encapsulated drug molecules on or near the surface of nanoparticles can quickly diffuse into solution and may lead to significant toxicity in vivo.[10] Burst release is especially severe when drug loading exceeds the encapsulation threshold of the polymer where there can be a significant amount of drug molecules precipitated on the surface of the nanoparticle.

Nanoencapsulates (NE) usually display a biphasic drug release pattern[10-12] with as high as 40-80% of the encapsulated drug molecules burst released during the first several or tens of hours.[10] After the first 24 to 48 hours, drug release becomes significantly slower due to the increased diffusion barrier for drug molecules buried more deeply in polymer nanoparticles. When these semi- or even completely empty nanoparticles eventually arrive and accumulate at the site where they are needed (e.g., tumor tissue), they usually have little or no remaining therapeutic efficacy.[6,13]

It is extremely difficult to achieve high drug loading with high encapsulation efficiency in polymeric nanoencapsulates. The encapsulation efficiency not only depends on the type, molecular weight and properties of the polymers used, but is also significantly affected by the chemical and physical properties of therapeutic molecules. For example, lower molecular weight polymers tend to exhibit lower encapsulation efficiency than higher molecular weight polymers. Hydrophilic molecules (e.g., doxorubicin) cannot be readily encapsulated into polymeric nanoparticles (Grovender T. et al. (1999) J. Controlled Release 57(2) 171-185). In all nanoencapsulates so far developed, drug loading (the weight percentage of drug in polymer nanoparticles) and encapsulation efficiency (percentage of drug encapsulated relative to total amount of drugs applied) vary dramatically from system to system and from batch to batch. For hydrophobic small molecules such as paclitaxel (Ptxl) or docetaxel (Dtxl), it is common that nanoparticle loading is in a range of 1 to 5 wt % and encapsulation efficiency varies from ~20- to 80%.[10,14]

Another problem encountered in nanoparticle drug encapsulation is undesirable particle heterogeneity. Nanoprecipitation of polymer and drugs, such as chemotherapeutics, frequently gives multimodal distributions as measured by dynamic light scattering, ranging from ~100 nm to 1 μm or higher. Particle heterogeneity may result because encapsulation involves distinct chemical species, a polymer and a drug molecule, with distinct molecular weights, flexibility and rigidity, hydrophobicity and tendencies toward forming crystals. Therefore it is likely the polymer and the drug molecule would tend to self-aggregate during nanoprecipitation leading to particle heterogeneity.

Nanoparticle materials exhibiting multimodal distributions are usually treated as having a different degree of aggregation of small nanoparticles with identical composition. However, this assumption may not always be correct. In a recent investigation on the effect of docetaxel loading at 1%, 5% and 10% on resulting PEG-b-PLGA nanoparticle size distributions (Cheng, J. et al. Formulation of functionalized PLGA-PEG nanoparticles for in vivo targeted drug delivery. Biomaterials 28, 869-76 (2007)), polydispersity of the particle preparations increased with docetaxel concentration from 0.154 for 1% loading to 0.203 for 5% loading and 0.212 for 10% loading. The size distribution of the nanoparticles exhibited a biphasic trend with a smaller diameter particle distribution accompanied by a distribution of larger diameter particles. The distribution corresponding to the smaller particles did not shift with the increase of drug concentration. The larger diameter locus of the two size distributions shifted higher as the drug loading increased (the size increasing from ~300 nm to ~1200 nm). Since the only difference between these formulations is the amount of drug loading, a significant amount of the nanoparticles formed may be due to aggregation of unencapsulated docetaxel due to its poor water solubility. In this work and that of others (Avgoustakis, K. et al. PLGA-mPEG nanoparticles of cisplatin: in vitro nanoparticle degradation, in vitro drug release and in vivo drug residence in blood properties. *J. Controlled Release* 79, 123-135 (2002)) on nanoprecipitation using polylactide and docetaxel, biphasic particle distributions were almost always observed.

It is desirable to develop a methodology to circumvent these difficulties, which will provide NPs with batch-to-batch consistency in encapsulation efficiency and drug loading. This invention provides a simple, one-step strategy for the preparation of drug-polymer (and drug-oligomer) conjugates which can be formed into nanoparticles with 100% encapsulation efficiency and predetermined drug loading. The nanoparticles formed by the methods herein employing drug conjugates are call nanoconjugates herein to distinguish over nanoencapsulates (NE). Further, the method of this invention can be broadly applied to provide polymer and oligomer conjugates of a variety of useful chemical species (bioactive species, drugs, reagents, diagnostics, contrast agents, reporter molecules, dyes, etc.) for the preparation of particulate delivery systems.

SUMMARY OF THE INVENTION

In one embodiment, this invention provides a one-step method for efficient preparation of certain drug-polymer (or oligomer) conjugates which are useful in the preparation of particles, including microparticles and nanoparticles, for delivery of the drug in vivo for therapeutic applications. The invention additionally provides certain drug-polymer and drug-oligomer conjugates which are useful in the preparation of particles for delivery of the drug in vivo. The invention also provides a method of making particulate drug delivery systems or vehicles employing the drug-polymer or drug-oligomer conjugates of this invention. The polymer and oligomer conjugates of this invention can be employed in any art-known method for the preparation of particles from polymers or oligomers. The methods herein are particularly useful for the preparation of nanoparticles for drug delivery and more particularly are useful for the preparation of nanoparticles for chemotherapy applications. Nanoparticles of this invention are, for example, prepared by nanoprecipitation methods from the polymer and/or oligomer conjugates described in this invention.

In specific embodiments, the invention provides particles containing a selected drug optionally for sustained or targeted drug delivery. In specific embodiments, a selected drug is substantially (90% or more by weight of the drug) covalently bound to polymer or oligomer in the particle. The particles are prepared, for example, by known methods from solutions containing drug-polymer and/or drug-oligomer conjugates. The drug conjugates of this invention are formed during polymerization of the polymer or oligomer in which the drug is employed as an initiator of the polymerization of the monomers which form the polymer and/or oligomer. More specifically, the drug conjugates are formed by ring-opening polymerization of cyclic monomers in the presence of an appropriate ring-opening polymerization catalyst and the initiator (the drug).

In specific embodiments, the drug-polymer or drug-oligomer conjugates of this invention are employed to make various types of particles useful for drug delivery containing the drug and ranging generally in size from about 2 nm to about 500 microns. In other more specific embodiments, the drug-polymer or drug-oligomer conjugates of this invention are employed to make microparticles containing the drug and ranging generally in size from about 500 nm to about 100 microns. In other embodiments, the drug-polymer or drug-oligomer conjugates of this invention are employed to make nanoparticles containing the drug and ranging generally in size from about 55 nm to about 600 nm. In other embodiments, the drug-polymer or drug-oligomer conjugates of this invention are employed to make particles containing the drug and ranging generally in size from about 2 nm to about 100 nm. In other embodiments, the drug-polymer or drug-oligomer conjugates of this invention are employed to make particles containing the drug and ranging generally in size from about 200 nm to about 800 nm. In other embodiments, the drug-polymer or drug-oligomer conjugates of this invention are employed to make particles containing the drug and ranging generally in size from about 1 micron to about 500 micron. In a specific embodiment, the methods of this invention can be employed to make nanoparticles in the 20-60 nm size range. Such nanoparticles can be made, for example by known micellation methods from polymer or oligomer conjugates as described herein followed by further reaction with a PEG-capping agent, for example PEG-isocyanate.

In another specific embodiment, the methods of this invention can be employed to make nanoparticles in the 1-20 nm range which are particularly useful for delivery to cells. Such nanoparticles are formed employing cyclic AB2 type monomers or mixtures of such monomers with other cyclic esters and carbonate monomers described herein above. AB2 type monomers polymerize in the methods herein to form hyperbranched or dendritic structures conjugated to a selected drug molecule. Particles formed directly by polymerization of the AB2 type monomers can be used for drug delivery. Alternatively, these particles can be subjected to surface treatments as discussed herein below.

The method of this invention is useful for forming polymer or oligomer conjugates with any small molecule drug (i.e., a small molecule drug is a non-peptide, non-sugar and non-nucleic acid-based drug) which contains at least one functional group which can function for initiation of the ring-opening polymerization reaction, e.g. a hydroxyl group or a thiol group. The drug may contain, but need not contain, a plurality of such polymerization initiation groups, e.g., a plurality of hydroxyl groups or thiol groups. In preferred embodiments, the drug contains only one of such polymerization groups. The hydroxyl groups may be primary, secondary or tertiary hydroxyl groups. Similarly, the thiol groups may be primary, secondary or tertiary thiol groups. The hydroxyl group may also be a phenolic hydroxyl group. In specific embodiments, the drug contains one or more non-phenolic hydroxyl groups.

In specific embodiments, the drug contains one or more non-phenolic hydroxyl groups which are primary or secondary hydroxyl groups. In specific embodiments, the drug contains a single non-phenolic hydroxyl group. In specific embodiments, the drug contains a single primary or secondary hydroxyl group. Exemplary drugs which can be employed in the methods herein are listed and illustrated in FIGS. 8 and 13 and additional drugs are listed below.

In specific embodiments, the drug is hydrophilic and in related embodiments, the drug is water-soluble (e.g., exhibiting solubility in water in the range of mg/mL). In other specific embodiments, the drug is hydrophobic and in related embodiments, the drug is not water-soluble or exhibits low water solubility (e.g., exhibiting solubility in water in the range of micrograms per mL or less).

In specific embodiments, the drug which is conjugated to the polymer or oligomer in the methods herein is a drug that is an anticancer agent or that is useful in chemotherapy. In specific embodiments, the drug is a taxane. In other specific embodiments, the drug is an anticancer agent of the anthracyclin family. In other embodiments, the drug is a protease inhibitor. In other specific embodiments, the drug is an inhibitor of reverse transcriptase. In other specific embodiments, the drug is an antiviral agent. In other specific embodiments, the drug is an antifungal agent. In other specific embodiments, the drug is a phenolic drug, i.e., having one or more phenolic hydroxyl groups. In other specific embodiments, the drug is a thiol drug, i.e., having one or more thiol groups.

The method of this invention is also useful for delivery of drugs which are peptides, proteins, sugars and/or nucleic acid (DNA or RNA). In each case, the drug must contain at least one functional group that can function as an initiator in the ring-opening polymerization reaction, e.g., at least one hydroxyl or one thiol group.

The method of this invention can be more broadly applied to any molecule or other chemical species (including synthetic, or naturally-occurring molecules and organic or inorganic species) which contains at least one functional group which can function as an initiator in a ring-opening polymerization reaction (e.g., a hydroxyl group or a thiol group) and which one wishes to administer or deliver in vivo using a particulate delivery system such as a microparticle or a nanoparticle. The method may be applied to form polymer or oligomer conjugates with any such useful chemical species including without limitation, reagents for diagnostic methods, nutrients or vitamins (which may also be considered drugs), or reporter molecules (e.g. radiolabeled or fluorescently labeled molecules). The chemical species to be conjugated to the polymer or oligomer may be hydrophilic, hydrophobic, water-soluble or water-insoluble. The chemical species may contain a plurality of hydroxyl groups or thiol groups which may be primary, secondary or tertiary hydroxyl groups and which may be phenolic hydroxyl groups. In specific embodiments, the hydroxyl groups are primary or secondary hydroxyl groups. In specific embodiments, the hydroxyl groups are phenolic hydroxyl groups. In specific embodiments, the thiol groups are primary or secondary hydroxyl groups. In specific embodiments, the chemical species is a chemical species other than a saccharide. In specific embodiments, the chemical species is a chemical species other than a carbohydrate.

In specific embodiments of all of the above-listed cyclic monomer, one or both of $Y_1$ and $Y_2$ are haloalkyl groups, particularly fluoroalkyl groups.

The scope of the invention as described and claimed encompasses the use of racemic forms of the cyclic monomers as well as the individual enantiomers and non-racemic mixtures thereof The methods herein employ any appropriate ring-opening polymerization catalyst which may be a metal-containing catalyst or an organocatalyst. In specific embodiments, the catalysts are selected from Mg(II) or Zn(II) catalysts. In other specific embodiments, 1,5,7-Triazabicyclo[4.4.0]dec-5-ene (TBD), N-methyl-TBD (MTBD), or 1,8-diazabicyclo[5.4.0]undec-7-ene (DBU) are employed as organocatalysts.

The molar ratio of combined monomer(s) to initiator(s) ranges most generally from 2:1 to 5000:1, and more specifically from 5:1 to 200:1 and yet more specifically from 10:1 to 100:1. In the methods herein two or more different cyclic monomers may be combined in the polymerization reaction to form copolymer conjugates. In the methods herein two or more different cyclic monomers may be sequentially added to the polymerization reaction to form block co-polymer conjugates. Two or more chemical species each having at least one hydroxyl or thiol group can be combined in the methods herein to provide a mixture of polymer or oligomer conjugates with the different chemical species. For example, two different drugs each having at least one hydroxyl group or thiol group may be combined in the polymerization method herein to form a mixture of polymer or oligomer drug conjugates. It can be beneficial, for example, to combine two or more drugs exhibiting different mechanisms of action for treatment of the same or related disorders, diseases or conditions.

In specific embodiments, particles, particularly nanoparticles, formed by the methods herein can exhibit drug loading (or more generally loading of the selected chemical species) that is 20% or more, 30% or more, 40% or more, or 50% or more.

In specific embodiments, particles, particularly nanoparticles, formed by the methods herein can exhibit long circulation lifetimes useful for effective in vivo delivery. This is particularly the case when the particles are surface modified employing methods described herein or employing methods that are known in the art. In specific embodiments, particles, particularly nanoparticles, formed by the methods herein can exhibit stability in salt solutions.

In the methods herein, formation of polymer or oligomer conjugates can be combined with any known method for the formation of particles, including nanoprecipitation, micellation, emulsion and double emulsion methods.

The invention also provides certain polymer or oligomer conjugates which are prepared by the polymerization methods herein. These conjugates can in general be those with any chemical species that it is desired to deliver in a particulate delivery system and particularly are drugs and most particularly are anticancer or chemotherapeutic drugs. In specific embodiments, the conjugates are those in which the polymer of the conjugate on average has 100 or fewer monomer units. In other embodiments, the conjugates are those in which the polymer of the conjugate has on average 75, 50, or 25 monomer units. In specific embodiments, the conjugates are those in which the polymer has weight average molecular weight of 5000 or less, 2500 or less, 1500 or less, or 1000 or less. In specific embodiments, the invention provides certain polymer or oligomer conjugates prepared by the polymerization methods herein and in which the chemical species of the conjugate is conjugated or bonded to only one polymer or oligomer. In specific embodiments, the invention provides certain polymer or oligomer conjugates prepared by the polymerization methods herein and in which the chemical species of the conjugate is conjugated or bonded to only one polymer or oligomer and at only one site in the chemical species.

In specific embodiments, the invention provides polymer or oligomer conjugates to hydrophilic chemical species, and in particular to hydrophilic drugs. In other specific embodiments, a hydrophobic chemical species, particularly a hydrophobic drug is conjugated to the polymer or oligomer.

The invention further provides particles, including microparticles and nanoparticles, comprising the polymer conjugates or oligomer conjugates of this invention which are useful for in vivo delivery of selected chemical species, more particularly one or more drugs and most particularly one or more anticancer or chemotherapeutic agents. In specific embodiments, the particles, including microparticles or nanoparticles are surface-modified by any means known in the art, for example, with one or more antibodies, with one or more nucleic acid molecules, e. g., aptamers, with one or more peptides or proteins, e.g., enzymes, with one or more polymers or oligomers, e.g., amphiphilic polymers, particularly amphiphilic polymers containing PEG. Surface-modification of particles as is known in the art can facilitate targeting of particles to certain tissue, can facilitate entry of particles into cells or can enhance stability of the particle. For example, nanoparticles formed from polyesters, polycarbonates or mixtures thereof can be coated with hydrophilic polymers such as PEG or amphiphilic polymers containing PEG to enhance circulation lifetime of the nanoparticle.

In additional embodiments, the invention provides particles having a core/shell structure or having a multiple layer structure in which at least one of the core or shell or one of the multiple layers is a layer which is formed from the drug (or other chemical species)-polymer/oligomer conjugates of this invention. In particular, the invention relates to nanoparticles having a core/shell structures in which the core or shell is formed from a polymer/oligomer conjugate of this invention. More specifically, nanoparticles can be formed with a core that is formed from a first polymer/oligomer conjugate and a shell that is formed from (1) a polymer, e.g., a hydrophilic polymer or an amphiphilic polymer or (2) a second polymer/oligomer conjugate of this invention. In specific embodiments, the first and second polymer/oligomer conjugates can be selected from those of a taxane, an anthracycline antibiotic, or a Shh antagonist which has a functional group, such as a hydroxyl or thiol group that can function for polymerization initiation as described herein. In more specific embodiments, the first and second polymer/oligomer conjugates can be selected from those of Ptxl, Dtxl, Doxo, cyclopamine, or camptothecin. The invention specifically provides multiple layer nanoparticles containing three or more different layers wherein at least one layer is formed from a polymer/oligomer conjugate of this invention. Nanoparticles include those having three, four or five layers. Nanoparticles include those in which all layers are formed from polymer/oligomer conjugates of this invention. Nanoparticles include those in which at least one layer is formed from a polymer/oligomer conjugate of this invention and at least one other layer is formed from a polymer (non-conjugated polymer) such as a hydrophilic, hydrophobic or amphiphilic polymer. In specific embodiments, nanoparticles include those in which at least one layer is formed from a polymer/oligomer conjugate of this invention and at least one other layer is formed from an amphiphilic polymer comprising PEG.

The invention additionally provides methods for making a medicament employing the polymer or oligomer conjugates of this invention as well as the medicaments made thereby. Medicaments are particles, particularly nanoparticles, formed from the conjugates of this invention.

The invention further provides kits for carrying out the polymerization reactions herein to form polymer or oligomer conjugates with a selected chemical species having at least one hydroxyl group. The kits comprise one or more containers which in turn comprise one or more cyclic monomers and one or more ring-opening polymerization catalysts and optionally include instructions for carrying out the polymerization reaction, instructions for making particles, one or more reagents or instructions for surface modification of particles, one or more solvents for carrying out the polymerization or for making particles, one or more control initiators, additional receptacles for carrying out the reaction, for forming particles or for carrying out surface modification. In specific embodiments, kits herein comprise a plurality of different cyclic monomers useful for making conjugates with different oligomers or polymers. In other embodiments, kits herein can further contain one or more different chemical species having at least one hydroxyl group for forming conjugates.

Additional embodiments of the invention will be apparent on review of the following detailed description, examples and figures.

BRIEF DESCRIPTION OF THE DRAWINGS

FIG. 10A is a graph illustrating the change in size of nanoparticles (nm) during a multidrug layer-by-layer precipitation process. In this process, a nanoconjugate formed by nanoprecipitation of a drug-polymer conjugate of this invention is treated with a second drug-polymer conjugate, under nanoprecipitation conditions, to form a shell or second layer of the second drug polymer in the nanoconjugates. The figure provides a size distribution plot of nanoparticle size change on the formation of a nanoparticle with a Dtxl-LA100 core and a Doxo-LA100 shell or second layer.

FIG. 10B is a plot of nanoparticle size (nm) as a function of the amount of shell-forming (second drug-polymer) conjugate on nanoprecipitation of a second drug polymer conjugate onto nanoparticles (NCs) formed from a first drug polymer conjugate. The plot compares size change as a function of the amount of the second drug-polymer conjugate added. In one case, the second drug conjugate is the same as the first drug conjugate and the plot illustrates the effect of adding increasing amounts of the same drug-polymer conjugate.

FIG. 11A shows results with addition of CA-LA10 and CA-LA25 where loading is indicated in parentheses. The figure shows that the EC50 of the cyclopamine NCs are significantly lower than that of free cyclopamine, demonstrating that the nanoconjugate allowed delivery, concentrated accumulation and release of cyclopamine in the targeted cells. FIG. 11B shows the results of culturing the Shh-Light2 cells with CA NCs along with NEs containing purmorphamine which is a Shh-agonist.

DETAILED DESCRIPTION

Figure 2A:
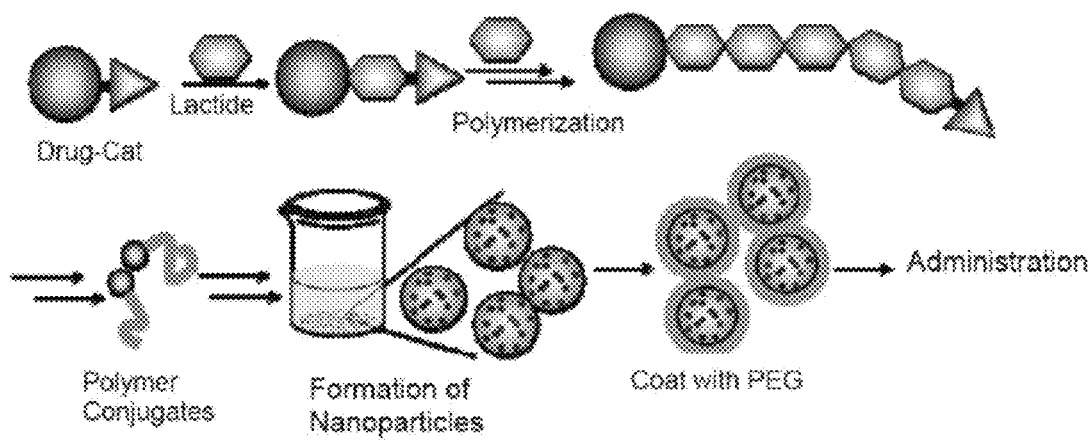
FIG. 2A is a schematic illustration of lactide polymerization of the invention exemplified for drug initiation of polymerization in the presence of catalyst for the preparation of high loading, 100% incorporation efficiency, controlled-releasing nanoconjugates for in vivo application.
Figure 2B:
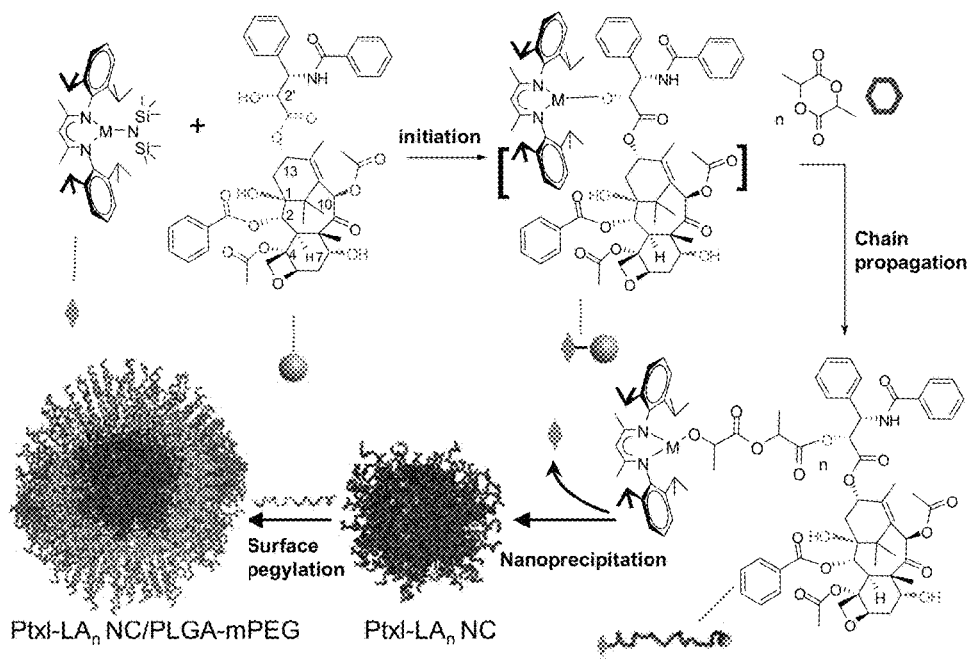
FIG. 2B provides a specific example of synthesis of exemplified pegylated pacitaxel-containing nanoconjugates by Ptxl initiated polymerization of lactide in the presence of $(BDI)MN(TMS)_2$ (where M=Mg or Zn), followed by nanoprecipitation and non-covalent surface pegylation with PLGA-mPEG. The polymerization is believed to be initiated through formation of a (BDI)M-oxide with Ptxl.

The present invention is based at least in part on the discovery that polymer and oligomer conjugates with drugs and other chemical species that can function as an initiator of ring-opening polymerization can be readily prepared in a single step polymerization synthesis in which the chemical species initiator is combined with one or more cyclic monomers and a ring-opening polymerization catalyst. FIG. 2A and FIG. 2B schematically illustrate the methods of this invention (A) and illustrates a specific example of nanoconjugate formation using paclitaxel conjugated to PLA. Further, it has been discovered that the polymer and oligomer conjugates thus formed are useful in the preparation of particles, including microparticles and nanoparticles, having particle sizes that are useful for the delivery of the chemical species in vivo. As specifically illustrated in FIG. 2A and FIG. 2B, nanoprecipitation methods can be used to form nanoparticles (nanoconjugates) containing the conjugates of this invention. As further illustrated in FIG. 2A and FIG. 2B nanoparticle nanoconjugates can be treated with PEG to peglyate the surface of the nanoparticle.

Polymer and oligomer conjugates formed by the methods herein are distinguishable from conjugates formed by conjugation of a chemical species, particularly a drug, with a pre-formed polymer. The conjugates formed can exhibit polymer average molecular weight much lower than pre-formed polymers. The conjugates formed can exhibit polydispersity must lower than pre-formed polymers. For example, polymer conjugates of this invention can exhibit polydispersities of 1.5 or less, 1.3 or less and 1.2 or less. In general the conjugates formed by the methods herein will be more uniform in polymer length than those formed by conjugation of a chemical species with a pre-formed polymer.

Figures 1A, 1B:
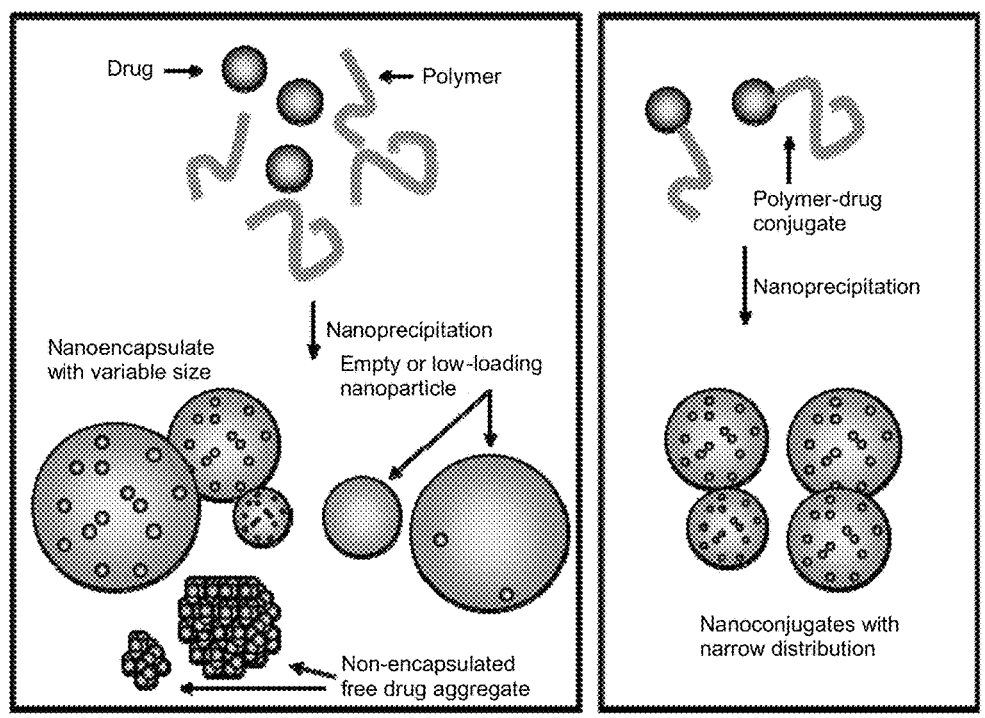
FIGS. 1A and 1B are schematic illustrations of the formation of nanoencapsulates (prior art) and nanoconjugates of this invention, respectively. The figures illustrate the structural differences between the nanoencapsulates and the nanoconjugates.

Nanoconjugates (NCs) formed from nanoprecipitation of the polymer or oligomer conjugates of this invention are distinguishable from nanoencapsulates (NEs) with respect to drug loading, drug encapsulation, drug release, particle distribution as well as ease of manufacture, as illustrated in FIG. 1. NEs exhibit low to medium drug loading (1-5 wt %), which it is not possible to predetermine and which can vary from batch to batch. NCs exhibit predefined drug loading levels with much higher batch to batch consistency. NEs exhibit uncontrollable encapsulation efficiency (ranging 10-80%), which vary from batch-to-batch, and system-to-system and which are unable to encapsulate hydrophilic drugs. NC's exhibit circa 100% encapsulation efficiency, with little or no batch-to-batch and system-to-system variation and can be formed with both hydrophilic and hydrophobic drugs. NEs exhibit significant burst release with 40-80% release in the first 24 hours. NCs exhibit little or no burst release of drug and provide for adjustable and controllable release of drug. NEs usually exhibit multimodal particle distributions. NCs exhibit monomodal particle distribution. The manufacture of NEs involves a multi-component/multi-step process which is difficult to scale up and detrimental for long-term storage. Further it is difficult to remove unencapsulated drug and requires difficult to use filtration method for sterilization. In contrast, the manufacture of NC involves a single component system which is straightforward to scale up and when properly stored, drug release should be minimal increasing storage lifetime. Because there is essentially no free drug or drug aggregate to remove, the method is simpler and less costly to implement.

During polymerization as illustrated in FIG. 2A, the chemical species that functions for polymerization initiation (e.g., drug) becomes covalently bonded to one or more growing oligomer or polymer chains. The polymerization reaction is a ring-opening polymerization reaction which preferably has the characteristics of a living polymerization. The invention has been exemplified herein with drugs and other chemical species having one or more hydroxyl groups or thiol groups which can function in the presence of certain catalysts as polymerization initiators. As discussed herein the ring-opening polymerization can employ various cyclic monomers, including cyclic esters, cyclic carbonates as well as cyclic siloxanes and cyclic phosphorous containing monomers. The polymerization can be exemplified for the polymerization of a lactide or glycolide and with a chemical species which is a drug and which carries one or more hydroxyl or thiol groups.

Figure 12:
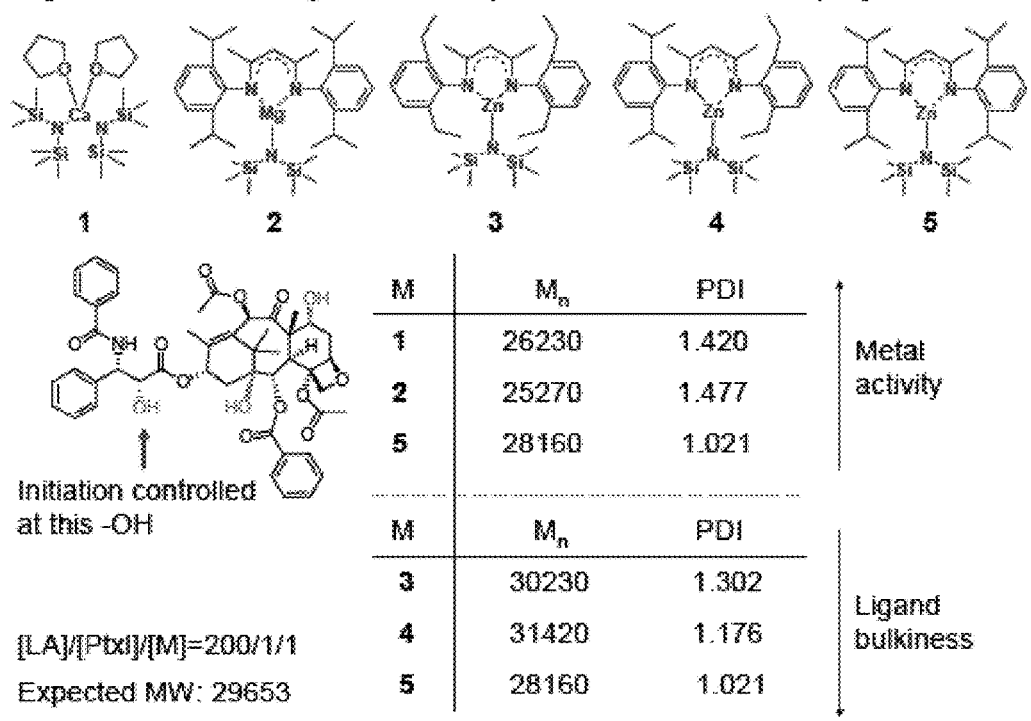
FIG. 12 provides the actual MW and PDI of Ptxl-LA conjugates, measured by GPC, formed using different catalysts (shown in the figure) in the LA polymerization synthesis of the conjugates.

Numerous alcohol-metal oxides (RO-M) have been developed for controlled, living polymerization of lactide and other related cyclic monomers with quantitative, terminal conjugation of RO to polylactide through an ester bond.[16] The amount of RO in the resulting polylactide can be precisely controlled by adjusting lactide/ROH ratio (e.g., the monomer to initiator molar ratio). In the present invention, ROH is a drug or other chemical species containing one or more hydroxyl groups that are to be conjugated to the polymer formed on ring-opening polymerization. A number of organocatalysts such as TBD (1,5,7-Triazabicyclo[4.4.0] dec-5-ene) can also be employed with hydroxyl or thiol containing initiators (i.e., drugs or other species to be conjugated) to form the conjugates of this invention. In these cases as well, the amount of the drug or other chemical species in the resulting polymer (or oligomer) is controlled by controlling the monomer/initiator ratio. Additional exemplary catalysts are provided in Example 6. The effect of varying catalyst on the actual MW of drug-polymer conjugates is illustrated in FIG. 12.

As part of this work, it was demonstrated that hydroxyl-containing chemotherapeutics could be quantitatively incorporated into polylactide using this polymerization method (exemplified with Ptxl in FIG. 2B using a Mg(II) complex ((BDI)MgN(TMS)$_2$ to activate Ptxl). As a consequence, drug release rate from the particle can be modulated by the cleavage of drug-polylactide ester bond, which is much more controllable than the diffusion of the encapsulated non-covalently bonded drug from a particle. Release kinetics of the drug would then be controlled by adjusting drug loading and particle size. Because polymerization reactions can be controlled to give quantitative yield, drug loading can in turn be precisely controlled simply by adjusting monomer/drug (or other species) molar ratio (monomer to initiator ratio). The capability of the present methods to precisely control drug loading by controlling the drug-polymer composition will significantly enhance clinical translation of the nanoparticle products and the likelihood for regulatory approval of the nanoparticles for clinic use. In addition, unprecedented high drug loading have been demonstrated (up to ~40%) with nanoparticles generated by the methods of this invention.

Nanoparticles can be formed from polymer and/or oligomer conjugates of this invention by various known methods. In a specific embodiment, nanoprecipitation is employed in which a solution of the conjugate is added to a solution in which the conjugate is insoluble. The precipitation step for forming nanoparticles employing the conjugates of this invention is simplified compared to the use of other starting materials because only one type of material, the conjugate is involved. The precipitation and encapsulation of a free drug in a polymer, even in a binary system, in contrast can be very complex. Control of integration of drug and polymer during phase separation is often poor especially when these two elements have distinct chemical and physical properties. Biphasic particle distributions have been consistently observed in nanoencapsulates which may be due in part to the self-aggregation of drug or polymer according to the like-dissolves-like principle. The method of this invention provides particles with monomodal particle distributions.

The benefits described above for drug-polymer or drug-oligomer conjugates will generally be observed in the formation of conjugates with any chemical species which can function as polymerization initiators and which it is desired to delivery in vivo in particulate form. Further, the specific benefits described above for the preparation of nanoparticle delivery compositions will generally be observed when the polymer or oligomer conjugates are employed to make any size particle that is useful for in vivo delivery.

Among various NP preparation methods, nanoprecipitation has been widely used for preparing NPs for use as encapsulated chemotherapy drugs. In a typical approach, a degradable hydrophobic polymer, such as polylactide, is mixed with a hydrophobic drug in a water-miscible solvent (e.g. THF or DMF) and added to excess water. Diffusion of the organic solvent into water facilitates the formation of sub-100 nm sized nano-aggregates with randomly mixed drug and polymer molecules. More generally any of the many methods that are known in the art for preparing nanoparticles from polymer or oligomeric materials can be employed with the conjugates of this invention.

In one aspect, the invention relates to a nanoconjugation technique which integrates drug-initiated cyclic ester (or carbonate) polymerization and nanoprecipitation to prepare drug-containing nanoparticles with pre-defined drug loading, near 100% encapsulation efficiency, minimized particle heterogeneity and significantly reduced burst release effect. In applications for cancer chemotherapy and particularly with nanoparticles useful in such therapy, particulate formulations of this invention will exhibit improved efficacy and decreased toxicity.

In an embodiment the invention relates to polymeric nanoparticles for cancer treatment. In this aspect of the invention, the drug-polymer or drug-oligomer conjugate includes an anticancer agent or chemotherapeutic agent. Nanoparticles useful for cancer treatment may contain a mixture of conjugates with two or more anticancer agents.

Particulate formulations (i.e., those containing NP and NC) of this invention can be administered to a subject by any known method appropriate for the size of the particle and the therapeutic, diagnostic or other agent carried in the particulate.

This invention additionally relates to the use of drug-conjugates with polymers and oligomers in the preparation of a medicament for in vivo delivery of the drug. The drug can, for example, be an anticancer agent. More specifically, the invention relates to the use of a drug in the manufacture of a medicament for treatment of cancer. In specific embodiments the medicament manufactured is in the form of particles, particularly nanoparticles, for administration in any appropriate dosage form. In specific embodiments, the medicament further comprises a pharmaceutically acceptable carrier or diluent and particularly a carrier or diluent suitable for the desired form of administration.

The term drug is employed herein very generically to include any chemical species that can provide therapeutic benefit to an individual in need of such benefit. Conjugates here can be formed with appropriate drugs or other chemical species which one wishes to deliver in a nanoparticle. The drug or other chemical species must have at least one functional group that can function in the presence of a catalyst for initiation of ring-opening polymerization. It is believed that the functional group must be capable of interaction with the catalyst to form a species active for polymerization. Hydroxyl groups and thiol groups, for example, are capable of functioning for initiation of ring-opening polymerization. Hydroxyl and thiol groups can be primary, secondary or tertiary functional groups. As is understood in the art, primary, secondary and tertiary hydroxyl and thiol group have different steric environments and can exhibit different relative reactivities.

In the description of chemical groups herein the terms used are intended to have their broadest art-recognized meaning.

Figure 13:
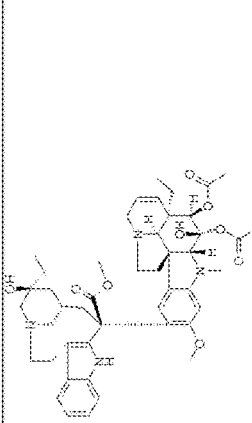
FIG. 13 is a partial list of drugs that are useful in the methods of the invention. The list includes structures.
Figure 13:
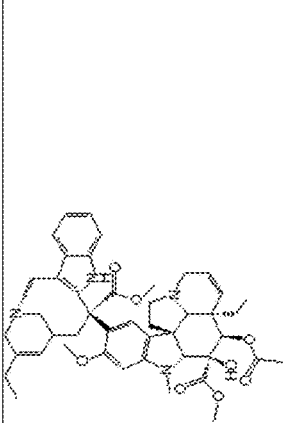
Figure 13:
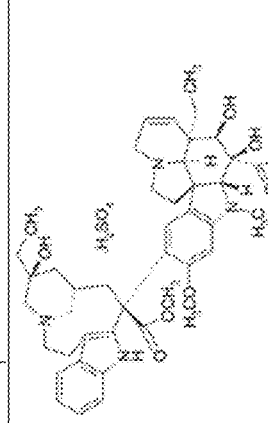
Figure 13:
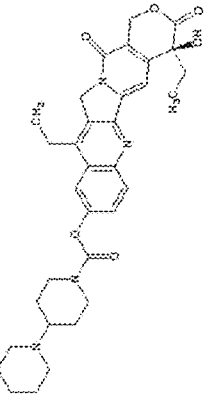
Figure 13:
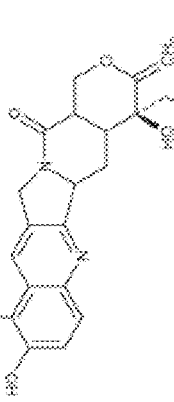
Figure 13:
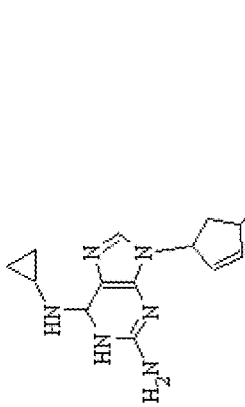

The chemical species having at least one functional group functional for initiation of ring-opening polymerization is combined with one or more cyclic monomers which can be polymerized by ring-opening polymerization and an appropriate ring-opening polymerization catalyst in an appropriate solvent under conditions and for a sufficient time to form oligomers or polymers as desired. A variety of chemical species are known to function for initiation of ring-opening polymerization in the presence of appropriate catalysts. Among these chemical species are those which contain one or more hydroxyl groups or one or more thiol groups in their chemical structure. The ability of a given chemical species to function for polymerization initiation as required for this invention can be readily assessed without undue experimentation in test polymerization reactions carried out employing materials and methods as taught herein or as well-known in the art. The methods of the invention have been, for example carried out successfully with drug and other species illustrated in FIG. 8. FIG. 13 contains a number of drugs containing hydroxyl groups that are useful in the preparation of drug-conjugates and nanoconjugate particles of this invention.

Additional drugs carrying hydroxyl groups which are useful in the methods of this invention include, among others, Darunavir (TMC-114), Tipranavir (TPV), Saquinavir (SQV), Ritonavir (RTV), Indinavir, Nelfinavir (NFV), Amprenavir (APV), Lopinavir (ABT-378), Atazanavir (ATV), Vinorelbine bitartrate, fulvestrant, Sarcodictyins, camptothecins, Vinblastine, bryostatin 1, (+)-Cylindricine, (+)-Lactacystin, Aeruginosin 298-A, (+)-Fostriecin, Garsubellin A/Hyperforin, (S)-Oxybutynin, Epothilone A, Zidovudine (AZT), Lamivudine (3TC), Didanosine (ddl), Abacavir (ABC), and Emtricitabine (FTC)

Additional drugs useful in the methods of this invention include those of various structures, but which have phenolic hydroxyl groups, which include among others include, bamethane, ethamivan, hexachlorophene, salicylanilide, pyrocatechin, thymol, pentazocine, phloroglucinol, eugenol, niclosamide, terbutaline, dopamine, methyldopa, norepinephrine, eugenol, α-naphthol, polybasic phenols, adrenaline, dopamine, phenylephrine, metaraminol, fenoterol, bithionol, alpha-tocopherol, isoprenaline, adrenaline, norepiniphrine, salbutamol, fenoterol, bithionol, chlorogenic acid/esters, captopril, amoxicillin, betaxolol, masoprocol, genistein, daidzein, daidzin, acetylglycitin, equol, glycitein, iodoresiniferatoxin, SB202190, and tyrphostin SU1498.

For a given chemical species that it is desired to conjugate by the method herein, it may be necessary to perform trial polymerizations employing different catalysts, for example, certain chemical species will be more compatible with organometallic catalysts, while others may be more compatible with organocatalysts. For example, it has been found that the chemical species even though containing appropriate functional groups may not function (or may have limited function) to initiate polymerization with certain metal-based catalysts because the chemical species may deactivate the catalysts. Specifically, conjugation of PLA with mitoxantrone employing (BDI)MgN(TMS)$_2$ did not proceed. It is believed that the mitoxantrone (Formula J) which has hydroxyalkyl amine groups may have deactivated the Mg catalyst.

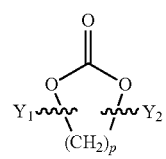

Formula J

Any of the cyclic monomers described herein including AB2 type cyclic monomers can be employed to form polymer or oligomer conjugates with such chemical species that can function for polymerization initiation. Any cyclic monomer or mixtures thereof that can be polymerized by ring-opening polymerization can be employed to form the drug-conjugates and particles, particularly nanoparticles, of this invention. In particular, cyclic monomers that can be polymerized by activated —OH or a metal-oxide group can in general be employed to form the drug-conjugates and particles of this invention. Useful cyclic monomers include cyclic esters and cyclic carbonates. Cyclic esters include, lactones, cyclic diesters, and cyclic ester-amides, e.g., cyclic depsipeptides.

Cyclic esters have the formula:

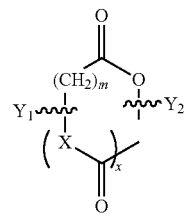

Formula A where m+n ranges from 1-20, X is O or NH, x is 0 or 1 to indicate the presence of the ester or amide group and $Y_1$ and $Y_2$ indicate the optional substitution of one or more carbon atoms of the ring with non-hydrogen substituents. Each $Y_1$ and $Y_2$, independently of one another are substituents that do not interfere with the polymerization reactions as described herein and can for example be selected from the group consisting of hydrogen, halogen, —COOR, —NRR', —SR, —OR, where R and R' independently are one or more hydrogens, alkyl or aryl groups, a guanidinium group, an imidiazole group, an alkyl group, alkenyl group, alkynyl group, aryl group (including phenyl or benzyl) and —N$_3$. Each $Y_1$ or $Y_2$ can also be an amino acid or short peptide having 1-5 amino acids. Each $Y_1$ or $Y_2$ also include groups as listed above which are protected with an art-recognized protecting group. Alkyl, alkenyl, alkynyl and aryl groups are optionally substituted with one or more halogens (including one or more fluorines), —N$_3$, —COOR", —NR"R'", —SR'", —OR" where R" and R' are independently hydrogen or an unsubstituted alkyl, alkenyl, alkynyl or aryl group. In a specific embodiment, one or two of $Y_1$ and $Y_2$ can be a hydroxyl alkyl group. In specific embodiments, each $Y_1$ and $Y_2$ is a hydrogen or an alkyl group having from 1 to 6 carbon atoms, particularly a methyl group.

Cyclic carbonates have the formula:

Formula B where p ranges from 1-20 and $Y_1$ and $Y_2$ indicate the optional substitution of one or more carbon atoms of the ring with non-hydrogen substituents and where each $Y_1$ and $Y_2$ are as defined above. In specific embodiments, each $Y_1$ and $Y_2$ is a hydrogen or an alkyl group having from 1 to 6 carbon atoms, particularly a methyl group. In a specific embodiment, one or two of $Y_1$ and $Y_2$ can be a hydroxyl alkyl group.

Cyclic esters include, without limitation, lactones such as β-butyrolactone (n=2), δ-valerolactone (n=4), ε-caprolactone (n=5), α-methyl-β-propriolactone, β-methyl-β-propriolactone, ω-pentadecalactone, ω-dodecalactone and any lactide or glycolide including all stereo-isomers thereof, e.g.

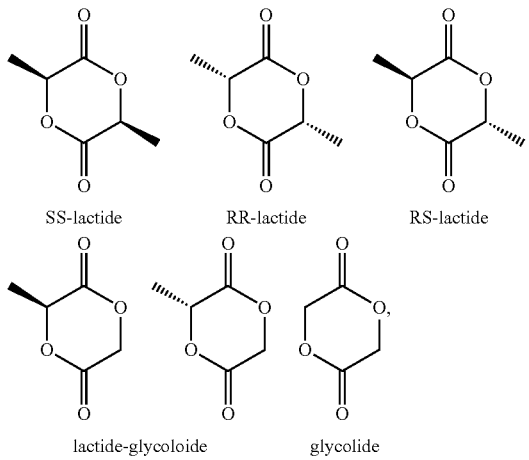

SS-lactide    RR-lactide    RS-lactide lactide-glycoloide    glycolide any substituted lactide or glycolide:

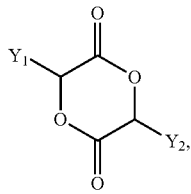

Formula C any cyclic depsipeptides (half-ester and half-amide) with 6 or 7 member ring structure, including, among others, Formulas D1-D3:

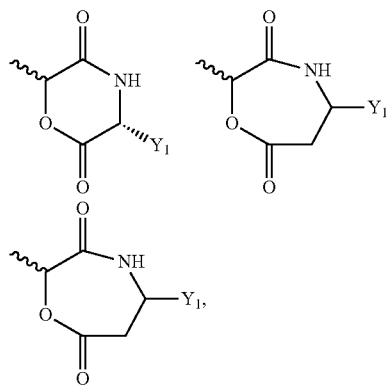

respectively.

Other cyclic monomers that are polymerizable by activated —OH or metal-oxide group, include phosphorus-containing cyclic esters including cyclic phosphates and phosphonites:

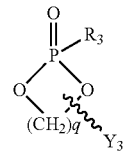

Formula E where q=1 to 20, $Y_3$ is as defined for $Y_1$ and $Y_2$ above and $R_3$ is $Y_3$ (phosphonates) or —$OY_3$ (phosphates).

Cyclic phosphonites:

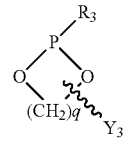

Formula F where variables are as defined above,
and silicon-containing cyclic monomers including

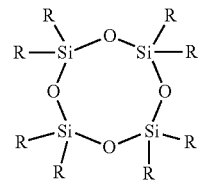

Formula G where each R is independently selected from hydrogen or an optionally substituted alkyl group. In specific embodiments of the above cyclic monomers, each of $Y_{1-3}$ are hydrogen or alkyl groups having 1-6 carbon atoms. In specific embodiments of the above cyclic monomers, all $Y_{1-3}$ are hydrogen or all $Y_{1-3}$ are alkyl groups having 1-6 carbon atoms, particularly all $Y_{1-3}$ are methyl groups. In specific embodiments of the above cyclic monomers, each R is selected from hydrogen or an alkyl group having 1-6 carbon atoms. In specific embodiments of the above cyclic monomers, all R's are hydrogen or all R's are alkyl groups having 1-6 carbon atoms, particularly all R's are methyl groups.

In specific embodiments, AB2 type cyclic polymerizable monomers are employed alone or in combination with other cyclic esters or cyclic carbonates. AB2 type cyclic ester monomers include those of formula:

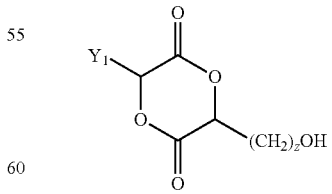

Formula H where z is 1 to 6 and $Y_1$ is as defined above. In specific embodiments, $Y_1$ can be hydrogen or an alkyl group having from 1-6 carbon atoms.

The term "alkyl" refers to a monoradical of a branched or unbranched (straight-chain or linear) saturated hydrocarbon and to cycloalkyl groups having one or more rings. Unless otherwise indicated preferred alkyl groups have 1 to 20 carbon atoms and more preferred are those that contain 1-10 carbon atoms. Short alkyl groups are those having 1 to 6 carbon atoms including methyl, ethyl, propyl, butyl, pentyl and hexyl groups, including all isomers thereof. Long alkyl groups are those having 8-20 carbon atoms and preferably those having 12-20 carbon atoms as well as those having 12-20 and those having 16-18 carbon atoms. The term "cycloalkyl" refers to cyclic alkyl groups having preferably 3 to 20 carbon atoms having a single cyclic ring or multiple condensed rings. Cycloalkyl groups include, by way of example, single ring structures such as cyclopropyl, cyclobutyl, cyclopentyl, cyclohexyl, cyclooctyl, and the like, or multiple ring structures such as adamantanyl, and the like. Unless otherwise indicated alkyl groups including cycloalkyl groups are optionally substituted as defined below.

The term "alkenyl" refers to a monoradical of a branched or unbranched unsaturated hydrocarbon group having one or more double bonds and to cycloalkenyl group having one or more rings wherein at least one ring contains a double bond. Unless otherwise indicated preferred alkyl groups have 1 to 20 carbon atoms and more preferred are those that contain 1-10 carbon atoms. Alkenyl groups may contain one or more double bonds (C=C) which may be conjugated or unconjugated. Preferred alkenyl groups are those having 1 or 2 double bonds and include omega-alkenyl groups. Short alkenyl groups are those having 2 to 6 carbon atoms including ethylene (vinyl), propylene, butylene, pentylene and hexylene groups including all isomers thereof. Long alkenyl groups are those having 8-20 carbon atoms and preferably those having 12-20 carbon atoms as well as those having 12-20 carbon atoms and those having 16-18 carbon atoms. The term "cycloalkenyl" refers to cyclic alkenyl groups of from 3 to 20 carbon atoms having a single cyclic ring or multiple condensed rings in which at least one ring contains a double bond (C=C). Cycloalkenyl groups include, by way of example, single ring structures (monocyclic) such as cyclopropenyl, cyclobutenyl, cyclopentenyl, cyclohexenyl, cyclooctenyl, cylcooctadienyl and cyclooctatrienyl as well as multiple ring structures. Unless otherwise indicated alkyl groups including cycloalkyl groups are optionally substituted as defined below.

The term "alkynyl" refers to a monoradical of an unsaturated hydrocarbon having one or more triple bonds (C≡C). Unless otherwise indicated preferred alkyl groups have 1 to 20 carbon atoms and more preferred are those that contain 1-10 carbon atoms. Alkynyl groups include ethynyl, propargyl, and the like. Short alkynyl groups are those having 2 to 6 carbon atoms, including all isomers thereof. Long alkynyl groups are those having 8-20 carbon atoms and preferably those having 12-20 carbon atoms as well as those having 12-16 carbon atoms and those having 16-18 carbon atoms. The term "cycloalkynyl" refers to cyclic alkynyl groups of from 3 to 20 carbon atoms having a single cyclic ring or multiple condensed rings in which at least one ring contains a triple bond (CC). Unless otherwise indicated alkyl groups including cycloalkyl groups are optionally substituted as defined below.

The term "aryl" refers to a monoradical containing at least one aromatic ring. The radical is formally derived by removing a H from a ring carbon. Aryl groups contain one or more rings at least one of which is aromatic. Rings of aryl groups may be linked by a single bond or a linker group or may be fused. Exemplary aryl groups include phenyl, biphenyl and naphthyl groups. Aryl groups include those having from 6 to 30 carbon atoms and those containing 6-12 carbon atoms. Unless otherwise noted aryl groups are optionally substituted as described herein. The term aryl includes "arylalkyl" groups which refers to a group that contains at least one alkyl group and at least one aryl group, the aryl group may be substituted on the alkyl group (e.g., benzyl, —CH$_2$—C$_6$H$_5$) or the alkyl group may be substituted on the aryl group (e.g., tolyl, —C$_6$—H$_4$—CH$_3$). Unless otherwise noted either the alkyl or the aryl portion of the arylalkyl group can be substituted as described herein.

The polymerization reaction to form conjugates of the invention can be carried out under various reaction conditions (temperature, solvent, concentrations) as is understood in the art. These conditions are in part selected to retain activity of any chemical species, particularly a drug, that is to be conjugated. The polymerization reaction can be carried out in any appropriate solvent or mixture of solvents. In a specific embodiment, the solvent is an anhydrous, water-miscible solvent. The polymerization can be carried out in the same or a different solvent than that which is used in the later preparation of particles. Useful solvents for the polymerization reaction include, among others, THF, acetone, methylene chloride, chloroform, dimethylformamide, DMSO, acetonitrile or mixtures thereof.

The term polydispersity is used herein to refer to the distribution of molecular weights of polymers in a given sample. The Polydispersity Index (PDI) is a specific measure of polydispersity and is the weight average molecular weight divided by the number average molecular weight and relates to the distribution of individual molecular weights in a given sample of polymers. PDI can be determined using Gel Permeation Chromatography (GPC). As the polymer chains in a given sample approach uniform chain length, PDI approaches 1.

Particles of this invention can be surface-modified as is known in the art to improve their usefulness as drug delivery vehicles.

For particles, particularly nanoparticles, that can successfully carry drug molecules or other chemical species to a desired in vivo location, e.g., a tumor site and get into cancer cells, it is preferably to well-control their features so that they can circumvent various physiology barriers to reach tumor tissues. Systemically administered nanoparticles without proper modification are usually cleared rapidly from the circulation and localized predominately in liver and spleen. Severe liver and spleen retention not only greatly diminishes the accessibility of the nanoparticles to target tissue, e.g., tumor tissue, but also causes liver and spleen damage. Clearance is due to the scavenging by liver Kupffer cells and spleen macrophages. Nanoparticles can be cleared within a few to tens of minutes by this passive and site-specific mechanism. In addition, nanoparticle surface characteristics and sizes play an important role in the blood opsonization, a process of the deposition of opsonins, like fibronectin, which will trigger immune responses and accelerate the clearance of nanoparticles from blood by macrophages. The binding of opsonins to the surface of nanoparticles can be substantially reduced when surface features of the nanoparticles are well controlled.

For example, nanoparticle surface pegylation, a well-established approach to reduce protein binding, forms a hydrophilic layer that can substantially reduce blood protein binding and reduce liver and spleen uptake. Pegylation creates stealth-like structures resembling the strategies developed by pathogenic microorganisms to bypass immune detection. Suppression of opsonization is thus achievable and has been utilized to enhance passive retention of nanoparticles in circulation and avoid trapping of nanoparticles in macrophages when they are in contact with blood. This simple strategy for manipulation of the nanoparticle surface can have a significant impact, as the circulation half-life of a nanoparticle can be increased from several minutes to several or tens of hours on pegylation. The use of surface pegylation has become a very popular approach to reduce recognition by macrophage cells.

Besides surface morphology, nanoparticle size is another important parameter that can significantly affect the biodistribution and in vivo efficacy. Nanoparticle sizes can dramatically affect the clearance rate. Large particles with size 200 nm or above are more likely to induce macrophage immune response and activate the uptake by Kupffer cells than their smaller counterparts. The size of fenestrae in the sinus endothelium in liver can be as large as 150 nm. Splenic filtration at interendothelial cell slits can predominate when particles size exceeds that of the cell slits (200-250 nm). Therefore nanoparticle sizes are usually controlled to 150 nm or below when they are to be used in anticancer drug delivery in order to have prolonged circulation. However, the nanoparticle size should not be too small, otherwise the particles can be very quickly filtered through the kidney (size <10 nm) which is a typical problem of polymer-drug conjugates with molecular weight of 40 kDa or lower. Very small particles (1-20 nm) can also slowly extravasate from the vasculature into the interstitial spaces, and are further accumulated in lymph nodes via lymphatic vessels. Nanoparticles with size smaller than 20 nm can readily escape from the vasculature into blood capillaries with open fenestration. Therefore nanoparticles must be large enough to prevent undesirable leakage from circulation, but must be small enough to minimize immune responses.

Most nanoparticles used for anticancer delivery are in the range of 20 to 150 nm. To improve anticancer delivery, attention has been focused on the development of stealth technologies to provide means for increased extravasation of long circulating NPs at leaky tumor vasculature. The vasculature of tumors is highly heterogeneous. Depending on the specific location, tumor tissue can be vascularly necrotic or extremely vascularized so that adequate nutrient and oxygen can be transported to the tumor tissue to support its fast growth. Tumor blood vessels are also very heterogeneous and have several abnormalities when compared to normal blood vessels. In general, tumor blood vessels are leakier than their normal counterparts, and are shown to have a characteristic pore cutoff size ranging between 380 and 780 nm. These pores become the pathway for NPs to leave the circulation system and enter the tumor interstitial space. Therefore NP with size of 150 nm or lower can freely diffuse through these leaky vessel pores, while particles with sizes larger than 400 nm are much less likely to extravasate into tumor issue. Because of the undeveloped lymphatic drainage system in tumor tissue, nanoparticles which extravasate the leaky pore of tumor vasculature cannot be readily removed. Therefore sustained circulation results in increased accumulation of nanoparticles over the time. This effect is the extremely well-known Enhanced Permeation and Retention (EPR) effect passive targeting mechanism in caner drug delivery.

The polymer and oligomer conjugates of this invention can be chemically modified by reaction to introduced desired terminal functional groups. Terminal functional groups of interest for applications to drug delivery include among others, hydroxyl, thiol, amine, azide, alkyne, alkene, ketone, phenol, halide, imidazole, guanidinium, carboxylate, or phosphate groups. These desired functional groups can be introduced at the terminus of the polymers or oligomers herein employing well known chemical methods. These functional groups can be employed to further conjugate the polymer or oligomer conjugate of this invention with other chemical species, such as other polymers, other oligomers, carbohydrates, peptides, proteins, antibodies, nucleic acids, aptamers etc. and/or to provide sites for surface modification for nanoparticles prepared using the conjugates of this invention.

The invention also relates to multiple layer particles in which a particle prepared by the methods herein is treated to coat or otherwise provide a second layer of polymer on the nanoparticle. The second polymer may be the same of different from that of the polymer of the polymer conjugate in the particle. Particles of this invention may contain two or more conjugated chemical species, e.g., two or more different drugs, that are compatible in a given application. Particles of the invention may contain different layers or portions in which the concentration of the chemical species or drug is different. For example an outer layer may contain a higher or lower concentration of a given chemical species (e.g., drug) compared to an inner layer. For example, an outer layer may contain PEG while an inner layer contains a conjugate of a different polymer. For example, a first inner layer can contain a polymer or oligomer conjugate of a first drug, and a second outer layer containing a polymer or oligomer conjugate of a second drug.

Nanoparticles of the invention can have a core/shell structure or have a multiple layer structure in which at least one of the core or shell or one of the multiple layers is a layer which is formed from the drug (or other chemical species)-polymer/oligomer conjugates of this invention. For example, as illustrated in examples herein the core of a nanoparticle can be formed form a polymer/oligomer conjugate of this invention by methods described above for forming nanoparticles. Thereafter a shell can be added to the core nanoparticle to generate a core/shell nanoparticle having increased particle size. More specifically, a core/shell nanoparticle can be formed with a core that is formed from a first polymer/oligomer conjugate and a shell that is formed from a polymer, e.g., a hydrophilic polymer or an amphiphilic polymer. In specific embodiments the polymer is an amphiphilic block co-polymer. In specific embodiments, the polymer is a polymer that is a PEG or which comprises a PEG (as the polymer or as a block of the polymer). Alternatively, a core/shell nanoparticle can be formed from a first polymer/oligomer conjugate of this invention (to form the core) and a second polymer/oligomer conjugate of this invention to form the shell. Note that in a specific embodiment, one of the first or second polymer conjugates can be one in which a label or reporter molecule is conjugated to the polymer or oligomer. In specific embodiments, the first and/or second polymer/oligomer conjugates can be selected from those of a taxane, an anthracycline antibiotic, or a Shh antagonist which has a functional group, such as a hydroxyl or thiol group that can function for polymerization initiation as described herein. In more specific embodiments, the first and/or second polymer/oligomer conjugates can be selected from those of Ptxl, Dtxl, Doxo, cyclopamine, or camptothecin.

Nanoparticles of the invention can be multiple layer nanoparticles containing three or more different layers wherein at least one layer is formed from a polymer/oligomer conjugate of this invention, including those of drugs or other chemical species, such as labels or reporter molecules. Nanoparticles include those having three, four or five layers. Nanoparticles include those in which all layers are formed from polymer/oligomer conjugates of this invention. Nanoparticles include those in which at least one layer is formed from a polymer/oligomer conjugate of this invention and at least one other layer is formed from a polymer (non-conjugated polymer) such as a hydrophilic, hydrophobic or amphiphilic polymer. In specific embodiments, nanoparticles include those in which at least one layer is formed from a polymer/oligomer conjugate of this invention and at least one other layer is formed from an amphiphilic polymer comprising PEG.

Polymers comprising PEG include among others amphiphilic copolymers comprising PEG such as poly(lactide)-PEG (PLA-PEG) an amphiphilic copolymer that has a PLA and PEG segment, poly(glycolide-co-lactide)-b-methoxylated PEG (PLGA-mPEG), an amphiphilic copolymer that has a PLGA and PEG segment. In such copolymers, PEG can, for example, range from 10% to 90%, from 20% to 50%, from 60% to 80%, from 50% to 75%, from 70% to 99% or from 1% to 50% of the copolymer.

Polymers and oliogmers used in the methods and materials herein are preferably biocompatible and biodegradable (dependent upon the desired application). They preferably exhibit little or no undesired toxicity in use.

The particles of this invention can be surface-modified for preferential targeting to certain cell types. Preferential targeting of particles can for example be achieved by covalent or non-covalent attachment of targeting ligands to the surface of the particle.

The term particle is used herein generally to refer to a particle having any given shape that has a size that is useful for in vivo delivery by some administration method. The particles may be micelles, aggregates, sphere or have no regular shape. The term particle size is used herein as it is generally used in the art and is determined by methods described in the Examples herein.

The invention relates to conjugates of polymers or oligomers. Most generally a polymer is a chemical species containing a plurality of repeating units which are bonded to each other. A polymer may contain more than one different repeating unit. The repeating unit typically derives from polymerization of a monomer. A copolymer specifically refers to a polymer containing two or more structurally different repeating units. The different repeating units of a polymer may be randomly ordered in the polymer chain or the same repeating units may be grouped into contiguous blocks in the polymer. When there are contiguous blocks of the two or more repeating units in a polymer, the polymer is a block co-polymer. As used herein the term polymer refers to a chemical species containing a total of more than 10 repeating units (there may be one or more repeating units). The term oligomer is used herein to refer to a chemical species having two to ten repeating units.

The conjugates of this invention are formed between a chemical species which has at least one hydroxyl group or one thiol group and oligomers or polymers formed by ring-opening polymerization. The chemical species must contain at least one functional group which under the conditions of the reaction functions as an initiator of the polymerization. The hydroxyl group can most generally be a primary (1'), secondary (2') or tertiary (3') hydroxyl group attached to a carbon, or a hydroxyl group attached to carbon of an aromatic ring which is generally described herein as a "phenolic hydroxyl group." Phenolic hydroxyl groups are those directly attached to a carbon of an aryl ring. The terms hydroxyl and hydroxy are used interchangeable herein. Hydroxyl groups do not include the OH moiety of —COOH groups (carboxylic acid groups) in which the hydrogen of the group is acidic. The hydrogens of phenolic hydroxyl groups are more acid than those of alcohols, but less acidic than those of carboxylic acid groups. The term hydroxyl as used herein also does not refer to —OH moieties which are bonded to N, P or S atoms. As is understood in the art a primary hydroxyl group is a hydroxyl group bonded to a carbon atom that is also bonded to two hydrogens (e.g., —$CH_2$—OH). A secondary hydroxyl group is a hydroxyl group bonded to a carbon atom that is bonded to one hydrogen atom (e.g. —CH(M)-OH, where M is an atom or group other than H, in many cases M is a carbon containing group. A tertiary hydroxyl group is a hydroxyl group bonded to a carbon atom that is not bonded to a hydrogen, typically the carbon bonded to the hydroxyl group is bonded to three other carbon atoms. The thiol group can most generally be a primary (1'), secondary (2') or tertiary (3') thiol group attached to a carbon, where the terms primary, secondary and tertiary are used as defined for the hydroxyl groups.

The particle formulation of this invention can be used to treat various diseases, disorders or conditions. Treatment methods of this invention comprise the step of administering a therapeutically effective amount of the drug to an individual in need of treatment in the form of nanoparticles prepared by the methods of this invention containing the drug. The term "therapeutically effective amount," as used herein, refers to the amount a given drug that, when administered to the individual in the particulate form, is effective to at least partially treat the disorder, disease or condition from which the individual is suffering, or to at least partially ameliorate a symptom of such disorder, disease or condition. As is understood in the art, the therapeutically effective amount of a given compound will depend at least in part upon, the mode of administration, any carrier or vehicle (e.g., solution, emulsion, etc.) employed, the specific disorder or condition, and the specific individual to whom the compound is to be administered (age, weight, condition, sex, etc.). The dosage requirements needed to achieve the "therapeutically effective amount" vary with the particular compositions employed, the route of administration, the severity of the symptoms presented and the particular subject being treated. Based on the results obtained in standard pharmacological test procedures, projected daily dosages of active compound can be determined as is understood in the art.

Particulate formulations herein can, for example, be in the form of dry powders which can be rehydrated as appropriate. The particulate formulations can be in unit dosage forms, e.g. in capsules, suspensions, dry powders and the like. In such form, the formulation can be sub-divided in unit dose containing appropriate quantities of the active ingredient; the unit dosage forms can be packaged compositions, for example, packaged powders, vials, ampoules, pre-filled syringes or sachets containing liquids. The unit dosage form can be, for example, a capsule, or it can be the appropriate number of any such compositions in package form.

The dosage employed can vary within wide limits and as is understood in the art will have to be adjusted to the individual requirements in each particular case. Any suitable form of administration can be employed in the method herein. The particles of this invention can be administered in oral dosage forms, intravenously, intraperitoneally, subcutaneously, or intramuscularly, all using dosage forms well known to those of ordinary skill in the pharmaceutical arts. Compounds of this invention can also be administered in intranasal form by topical use of suitable intranasal vehicles. For intranasal or intrabronchial inhalation or insulation, the compounds of this invention may be formulated into an aqueous or partially aqueous solution, which can then be utilized in the form of an aerosol.

The present invention provides methods of treating disorders, diseases conditions and symptoms in a mammal and particularly in a human, by administering to an individual in need of treatment or prophylaxis, a therapeutically effective amount of a particulate formulation of this invention to the mammal in need thereof. The result of treatment can be partially or completely alleviating, inhibiting, preventing, ameliorating and/or relieving the disorder, condition or one or more symptoms thereof. Administration includes any form of administration that is known in the art to be effective for a given type of disease or disorder, and is intended to encompass administration in any appropriate dosage form. An individual in need of treatment or prophylaxis includes those who have been diagnosed to have a given disorder or condition and to those who are suspected, for example, as a consequence of the display of certain symptoms, of having such disorders or conditions.

The term drug includes "pharmaceutically acceptable salts" of drugs as well as prodrugs The term "prodrug," as used herein, means a compound that is convertible in vivo by metabolic means (e.g. by hydrolysis) to a drug.

Particles of the invention can be surface modified by any known method to improve their surface properties for in vivo delivery or other applications. Particle surfaces can be modified for example by pegylation as is known in the art. Particle surfaces can be modified by coating with a polymer as is known in the art.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. A number of specific groups of variable definitions have been described herein. It is intended that all combinations and subcombinations of the specific groups of variable definitions are individually included in this disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Isotopic variants, including those carrying radioisotopes, may also be useful in diagnostic assays and in therapeutics. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein. References cited herein are incorporated by reference herein to provide additional cyclic monomers, additional catalysts, additional reaction conditions, additional drugs and other chemical species having at least one hydroxyl group, additional surface treatment or modification methods and reagents and additional applications of the methods, compositions and kits of this invention.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, e.g., cyclic monomers, drugs and other chemical species having at least one hydroxyl group, biological materials, reagents, e.g., ring-opening polymerization catalysts, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

EXAMPLES

Example 1

Polylactide-Paclitaxel Nanoconjugate Particles

Nanoparticle design of this invention is based on the use of drugs as initiators in ring-opening polymerization reactions to form drug-polymer (and drug-oligomer) conjugates in which the drug is covalently bonded to the polymer or oligomer. Because the drug is used as the initiator of polymerization, the efficiency of conjugation of the drug to the polymer (oligomer) will be very high, ideally 100%. Additionally, if all of the drug molecules are efficiently incorporated into a living polymerization (e.g. where drug molecules function as initiators), the drug loading percentage can be precisely controlled by adjusting the monomer/initiator ratio.

To initially demonstrate this strategy, paclitaxel (Ptxl) was used in the presence of an appropriate catalyst to initiate a living polymerization of lactide. Utilization of molecules containing hydroxyl groups as initiators for the ring-opening living polymerization of lactide is well established. Paclitaxel, the best selling chemotherapy drug in the U.S., contains three hydroxyl groups.

Metal-oxides (M-ORs) are well-known initiators for living ring-opening polymerizations of cyclic esters, such as DL-lactide (LA) used in this study. They can be prepared in situ by mixing a hydroxyl-containing compound with an active metal complex, such as a metal-amido compound (B. M. Chamberlain, M. Cheng, D. R. Moore, T. M. Ovitt, E. B. Lobkovsky, G. W. Coates, *J. Am. Chem. Soc.* 2001, 123, 3229). The in situ formed M-ORs can initiate controlled, living polymerization of LA, resulting in quantitative incorporation of OR to the PLA terminals and 100% monomer conversions. It was found that Ptxl can be incorporated into polyesters through metal-Ptxl oxide mediated polymerization of LA. Drug loadings can thus be precisely controlled by adjusting LA to Ptxl ratios. The incorporation efficiency of Ptxl to the resulting PLA should be 100% as the formation of metal-OR is usually instantaneous and quantitative. After polymerization, Ptxl molecules are covalently linked to the terminals of PLA through a hydrolysable ester linker and are subject to sustained release upon hydrolysis. The Ptxl-PLA conjugates are employed in nanoprecipitation to generate polymeric NPs, Nanoconjugates (NC) containing covalently linked Ptxl.

To ensure a rapid and complete polymerization of LA (lactide) at room temperature (BDI)MgN(TMS)$_2$ (Chamberlain, et al. 2001 supra) a very active catalyst for the polymerization of LA was employed. (See: FIG. 2B for structure of the catalyst.) Ptxl was mixed with 1 eq. (BDI)MgN(TMS)$_2$ and the polymerization of LA was completed within minutes at room temperature with nearly quantitative incorporation of Ptxl into the resulting PLA (Table 1). It is believed that an in situ formed (BDI)Mg-Ptxl complex (structure uncharacterized; possibly a monomeric Mg-Ptxl oxide) initiated polymerization.

The Ptxl incorporated into the polymer conjugate was released to its original form and other degradation species after the Ptxl-PLA was treated with 0.1-1 M NaOH, which demonstrated that Ptxl was conjugated to PLA through a hydrolysable ester bond.

Nanoprecipitation of the Ptxl-PLA conjugates resulted in sub-100 nm NPs (Table 1). To be differentiated from NEs, these NPs derived from nanoprecipitation of Ptxl-PLA conjugates are called nanoconjugates (NCs). Specific conjugated polymers are named herein as Drug (or other chemical species)-LA$_n$, where the drug or other chemical species is indicated by a shortened form (e.g., Ptxl, Dtxl, Doxo, Pyr or Cy5), and PLA is denoted as LA$_n$ where n is the M/I ratio. In some cases, NC's, i.e., nanoprecipitates formed from the conjugated polymer are named NC of Drug-LA$_n$. The use of these terms is clear from the context of their use.

NCs with monomodal particle distributions and low polydispersities were consistently obtained through the nanoprecipitation of Ptxl-PLA conjugates. Because the multimodal distribution of NEs is due in part to the aggregation of the non-encapsulated free drug (J. Cheng, B. A. Teply, I. Sherifi, J. Sung, G. Luther, F. X. Gu, E. Levy-Nissenbaum, A. F. Radovic-Moreno, R. Langer, O. C. Farokhzad, *Biomaterials* 2007, 28, 869), the monomodal distribution observed with NCs is likely related to the unimolecular structures of Ptxl-PLA conjugates from which they are made.

Both the solvent and the concentration of polymer have dramatic effect on the sizes of NPs prepared by nanoprecipitation. Solvent that has higher water-miscibility (e.g., DMF) tends to diffuse into water faster than a solvent with lower water-miscibility (e.g., THF or acetone) (Cheng et al, 2007, supra). When a hydrophobic polymer in a highly water-miscible solvent is added to water, fast nucleation of polymer aggregation is anticipated. Thus, the increased numbers of particles due to rapid nucleation lead to reduced particle sizes when the concentration of polymer remains unchanged in solution. When the solvent type and the solvent/water ratio are fixed, the particle sizes usually show a linear correlation with the polymer concentrations because the number of particles remain roughly unchanged at that condition.

TABLE 1

Formation of drug-PLA nanoconjugates (NC) with high loadings, high incorporation efficiencies, small particle sizes and low particle distributions

| Entry | NC | M/I$^a$ | Load (wt %) | Lactide$^b$ Conver. | IE$^c$ | Particle Size + SD(nm)$^d$ | Polydispersity + SD$^{d,e}$ |
|---|---|---|---|---|---|---|---|
| 1 | Pyr-LA$_{100}$ | 100 | 1.6 | >99% | >99% | 101.0 ± 1.4 | 0.09 ± 0.01 |
| 2 | Pyr-LA$_{50}$ | 50 | 3.1 | >99% | >99% | 107.7 ± 2.2 | 0.07 ± 0.01 |
| 3 | Pyr-LA$_{25}$ | 25 | 6.1 | >99% | >99% | 102.2 ± 1.0 | 0.06 ± 0.01 |

TABLE 1-continued

Formation of drug-PLA nanoconjugates (NC) with high loadings, high incorporation efficiencies, small particle sizes and low particle distributions

| Entry | NC | M/I[a] | Load (wt %) | Lactide[b] Conver. | IE[c] | Particle Size + SD(nm)[d] | Polydispersity + SD[d,e] |
|---|---|---|---|---|---|---|---|
| 4 | Ptxl-LA$_{100}$ | 100 | 5.6 | >99% | >99% | 95.1 ± 2.7 | 0.04 ± 0.01 |
| 5 | Ptxl-LA$_{50}$ | 50 | 10.6 | >99% | >99% | 80.6 ± 0.2 | 0.05 ± 0.01 |
| 6 | Ptxl-LA$_{25}$ | 25 | 19.2 | >99% | 97% | 55.6 ± 0.5 | 0.04 ± 0.01 |
| 7 | Ptxl-LA$_{15}$ | 15 | 28.3 | >99% | 95% | 85.5 ± 1.4 | 0.09 ± 0.03 |
| 8 | Dtxl-LA$_{100}$ | 100 | 5.3 | >99% | >99% | 84.7 ± 0.5 | 0.05 ± 0.02 |
| 9 | Dtxl-LA$_{25}$ | 25 | 8.3 | >99% | 98% | 64.5 ± 0.7 | 0.05 ± 0.02 |
| 10 | Dtxl-LA$_{10}$ | 10 | 35.9 | >99% | 95% | 77.9 ± 1.5 | 0.06 ± 0.02 |
| 11 | Doxo-LA$_{100}$ | 100 | 3.6 | >99% | >99% | 96.3 ± 0.7 | 0.082 ± 0.011 |
| 12 | Doxo-LA$_{50}$ | 50 | 7.0 | >99% | >99% | 101.6 ± 0.6 | 0.075 ± 0.011 |
| 13 | Doxo-LA$_{25}$ | 25 | 13.1 | >99% | >98% | 90.8 ± 0.9 | 0.088 ± 0.010 |
| 14 | Doxo-LA$_{10}$ | 10 | 27.4 | >97% | >94% | 125.2 ± 2.3 | 0.110 ± 0.014 |

[a]M/I = monomer/initiator ratio. For all samples, they are first dissolved in DMF and dropwise added into water under rapid stirring;
[b]Determined by analyzing unreacted lactide using FTIR (1771 cm−1);
[c]Incorporation Efficiency. Based on RP-HPLC analysis of free molecules. Incorporation efficiency is used instead of encapsulation efficiency as drug molecules are conjugated to, not encapsulated in, polylactide;
[d]Determined by dynamic light scattering, SD = standard deviation;
[e]When polydispersity is measured by the dynamic light scattering machine, the value is a statistical index to indicate the dispersity of the particle size.

Nanoprecipitation of Ptxl-PLA conjugates followed these trends. At fixed concentration of Ptxl-PLA conjugate, the sizes of NCs prepared by precipitating a DMF solution of Ptxl-PLA conjugate are typically 20-30 nm smaller than those prepared with acetone or THF as solvent. When nanoprecipitation was carried out using DMF as solvent at a DMF/water ratio of 1/20 (v/v), the size of Ptxl-LA$_{200}$ NCs showed a linear correlation with the concentration of Ptxl-LA$_{200}$ conjugate, and can be precisely tuned from 60 nm to 100 nm by changing the concentration of Ptxl-LA$_{200}$. Similar linear correlations were observed when nanoconjugates were formed with other drug-polymer conjugates by nanoprecipitation.

Compared with the conventional nanoprecipitates in which drug loading and encapsulation efficiency can be extremely low in smaller particles, the nanoconjugates prepared by the method herein should all contain exactly the same density of drug (e.g., Ptxl) in polymer matrix because the polymer-conjugate drug loading remains unchanged during nanoprecipitation.

Figure 3:
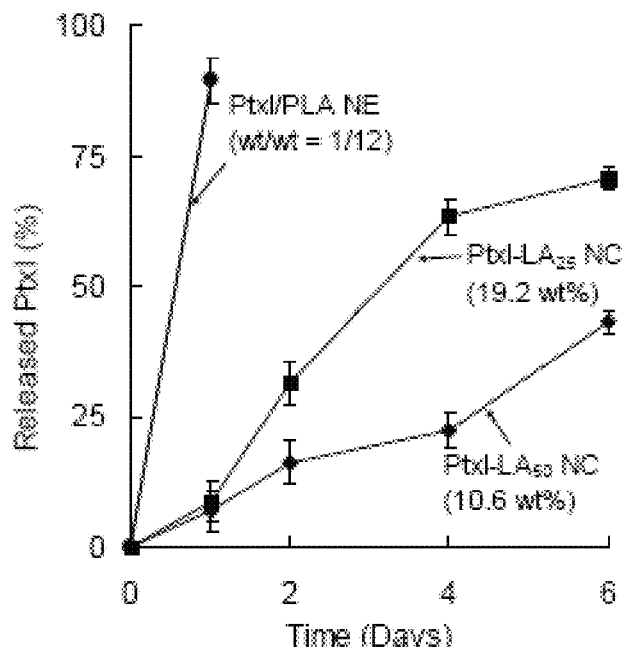
FIG. 3 is a graph of the release kinetics at 37 C in 1×PBS of Pxtl from Pxtl-LA nanoconjugates: Pxtl-LA25 NC and Pxtl-LA50 NC (drug loading indicated in figure). Also included in the graph for comparison is the release kinetics of a Pxtl/PLA nanoencapsulate (NE) prepared by nanoprecipitating a mixture of Ptxl and PLA (Pxtl/PLA (wt/wt)=1/12).

Drug burst release causes undesired side-effect and reduced therapeutic efficacy in nanoencapsulates. Since the Ptxl release kinetics of Ptxl-PLA NCs is determined by both the hydrolysis of the Ptxl-PLA ester linker and the drug diffusion, the release kinetics of Ptxl from NCs should be more controllable with significantly reduced burst release effect. Well-controlled Ptxl release was observed in NCs (FIG. 3). Ptxl released from Ptxl-LA50 (10.6 wt %) and Ptxl-LA25 (19.2 wt %) were 7.0% and 8.7% at Day 1, and 43% and 70.4% at Day 6, respectively. In comparison, 89% of Ptxl was released within 24 hrs from Ptxl/PLA NE (FIG. 3). The release of Ptxl from Ptxl-LA$_{50}$ NC was slower than that from Ptxl-LA$_{25}$ NC, presumably because of the higher MW of Ptxl-LA$_{50}$ and more compact particle aggregation. In fact, lower-loading NCs displaying slower drug release were observed in all drug-PLA NCs that were studied.

Figure 4:
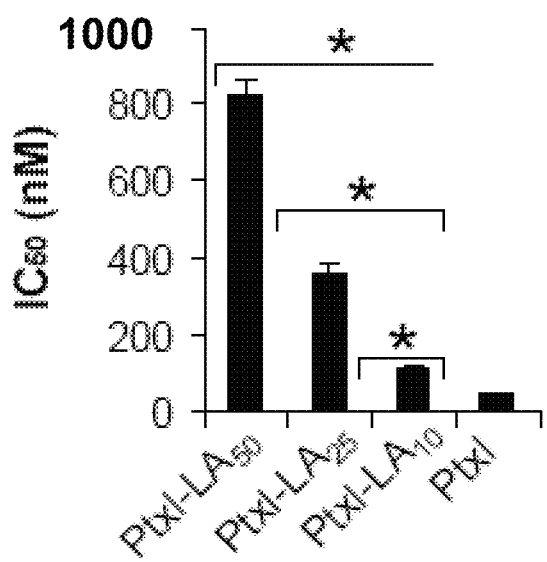
FIG. 4 is a graph showing toxicity evaluation of Ptxl-LA50 NC, Ptxl-LA25 NC, Ptxl-LA$_{10}$ NC and Pxtl using the MTT assay in PC-3 cells after 24 h incubation. The "*" indicates significance at 95% confidence interval.

The in vitro toxicities of NCs are determined by the amount of Ptxl released; they thus show strong correlation with drug loadings (FIG. 4). The IC$_{50}$s of Ptxl-LA$_{15}$, Ptxl-LA$_{25}$ and Ptxl-LA$_{50}$ NCs with similar sizes (~100 nm), determined by MTT assays in PC-3 cells, are 111, 370 and 855 nM, respectively. The Ptxl-LA$_{15}$ NC has nearly identical IC$_{50}$ as free Ptxl (87 nM); while the IC$_{50}$ of the Ptxl-LA$_{50}$ NC is an order of magnitude higher. As a result, the toxicity of NCs can be tuned in a wide range simply by controlling NC drug loading.

Surface modification of NPs with poly(ethylene glycol) (PEG) is a widely used approach for prolonged systemic circulation of NPs and reduced NP aggregation in blood. (P. Caliceti, F. M. Veronese, Advanced Drug Delivery Reviews 2003, 55, 1261; R. Gref, Y. Minamitake, M. T. Peracchia, V. Trubetskoy, V. Torchilin, R. Langer, Science 1994, 263, 1600.)

A non-covalent approach to pegylate the NC surface was initially employed to reduce the efforts of removing unreacted reagents and by-products. For example, poly (glycolide-co-lactide)-b-methoxylated PEG (PLGA-mPEG), an amphiphilic copolymer that has a 13 kDa PLGA and a 5 kDa PEG segment was used to pegylate the NCs. It has been reported by Pierri et al. (Journal of Biomedical Materials Research Part A; 2005; 639-647) that the micellation of amphiphilic copolymer PLA-b-PEG can be significantly eliminated when PEG is above 70% or below 50% of the hydrophobic block.

Figure 5:
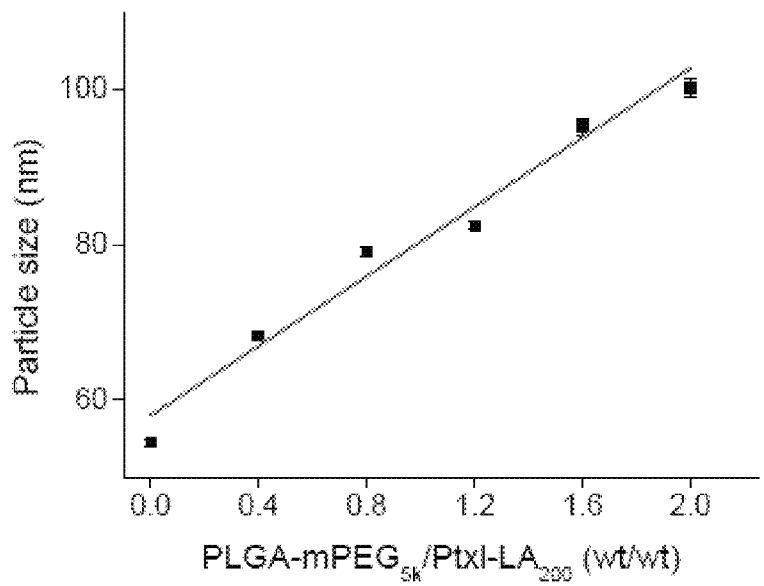
FIG. 5 is a graph showing changes in particle size when PLGA-mPEG$_{5k}$ is added to Pxt-LA200 NC. Particle size increases linearly as a function of the weight ratio of amphiphilic copolymer to drug-polymer conjugate.

It is expected that the PLGA block forms strong interaction with NCs through hydrophobic interaction to create a stable PEG shell. Similar approach has been used previously in NP surface pegylation. (X. H. Gao, Y. Y. Cui, R. M. Levenson, L. W. K. Chung, S. M. Nie, Nat. Biotechnol. 2004, 22, 969). Sequential addition of 0.4 to 2 equivalent (in mass) of PLGA-mPEG to Ptxl-LA$_{200}$ resulted in a linear increase in particle size from 54.5 nm to 100.3 nm (FIG. 5).

Figure 6:
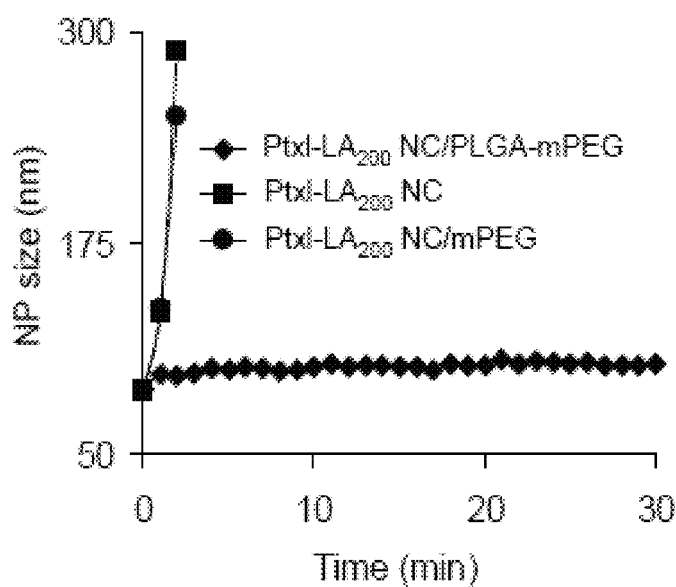
FIG. 6 is a graph illustrating the stability of Ptxl-LA200 NC in PBS at 37 C before (■) and after treatment with PLGA-mPEG5K (♦) or mPEG$_{5k}$ (●).
Figure 7A:
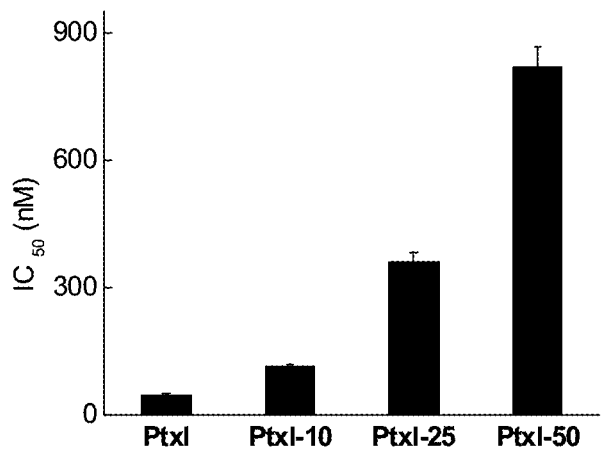
FIGS. 7A-D are graphs showing the results of MTT studies of Ptxl-LA, Dtxl-LA, CPT-LA and Doxo-LA NCs cytotoxicity on PC-3 prostate cancer cells.
Figure 7B:
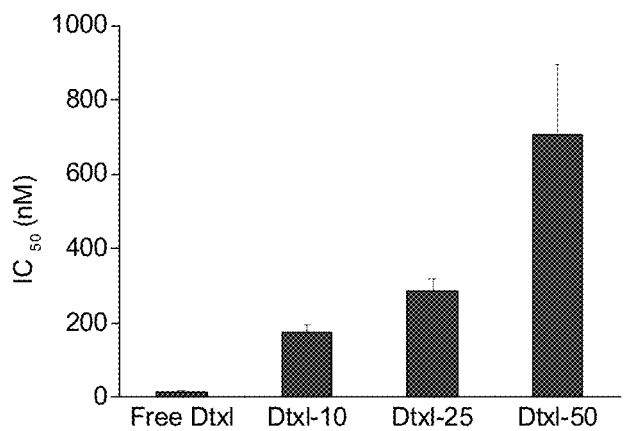
Figure 7C:
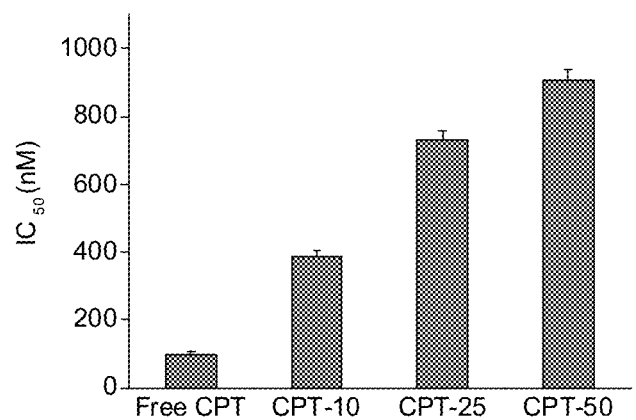
Figure 7D:
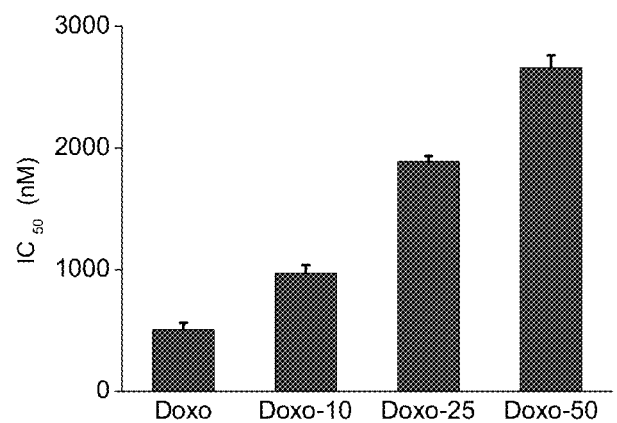

The PLGA-mPEG modified Ptxl-LA$_{200}$ NCs showed significantly enhanced stability in PBS compared to the untreated NCs or NCs treated only with mPEG (FIG. 6), indicating the importance of the hydrophobic PLGA segment to the non-covalent interaction between PLGA-mPEG and NCs. NCs are subject to instantaneous dilution after intravenous administration, which may result in dissociation of PLGA-mPEG from NCs. However, sequential dilution of the PLGA-mPEG treated Ptxl-LA$_{200}$ NCs from 1 mg/mL to 0.01 mg/mL did not show any increase in particle size in PBS. This study indicates that the PEG shells formed as described above should remain tightly bound to the NCs in systemic circulation.

Surface coating of NCs with PEG can lead to formation of long circulating nanoparticles. The linear increase of nanoparticle size observed when PLA-PEG was added to the Ptxl-PLA nanoparticles indicates the formation of a layered structure on the surface of the nanoparticle because of the hydrophobic interaction of PLA-PEG and PLA-paclitaxel. PEG corona were formed readily. Nanoparticles generated using this method are stable in salt solution. The simple strategy of making salt-stable nanoparticles will make the nanoparticles readily transferable to systemic study.

PEG can also be covalently conjugated to the NCs as is known in the art. (O. C. Farokhzad, J. J. Cheng, B. A. Teply, I. Sherifi, S. Jon, P. W. Kantoff, J. P. Richie, R. Langer, *Pro. Nat'l Acad. Sci. USA* 2006, 103, 6315).

Ptxl has three hydroxyl groups at its C-2', C-1 and C-7 positions, respectively. Each of these three hydroxyl groups can potentially initiate LA polymerizations, resulting in Ptxl-PLA conjugates with 1 to 3 PLA chains attached to Ptxl. To reduce the heterogeneity of Ptxl-PLA, it is preferred that Ptxl-PLA conjugate containing a single PLA chain. It has been found that polymerization initiation can be controlled at a specific hydroxyl group of the drug (e.g., Ptxl) to make the PLA conjugate containing a single PLA chain.

The three hydroxyl groups of Ptxl differ in steric hindrance in the order of 2'-OH<7-0H<1-0H. The tertiary 1-OH is least accessible and typically is inactive. (D. Mastropaolo, A. Camerman, Y. G. Luo, G. D. Brayer, N. Camerman, *Proc. Natl. Acad. Sci. U.S.A.* 1995, 92, 6920.) The 7-OH, however, could potentially compete with the 2'-OH, the most accessible and active hydroxyl group of Ptxl, for complexing with metal catalyst. In view of the difference in steric hindrance at the different OH groups, it was postulated that employing a catalyst with bulky groups, e.g., a metal catalyst with a bulky chelating ligand might differentiate between 2'- and the 7-OH, and thus preferentially or even specifically form Ptxl-metal complex through the 2'-OH for LA polymerization.

Attempts using NMR to determine to which hydroxyl group(s) the PLA chains were attached were unsuccessful because of the complexity of the material. To determine if PLA was attached to the 2'-OH or the 7-OH, the Ptxl of Ptxl-PLA was reacted with tetrabutylammonium borohydride ($Bu_4NBH_4$). This reagent is reported (N. F. Magri, D. G. I. Kingston, C. Jitrangsri, T. Piccariello, *J. Org. Chem.* 1986, 51, 3239) to quantitatively reduce the 13-ester bond of Ptxl into Baccatin III (BAC) and (1S,2R)-N-1-(1-phenyl-2,3-dihydroxypropyl)benzamide (PDB). BAC contains the 7-OH of PTxl, while PDB contains the 2'-OH of Pxtl.

Ptxl-LA5 was prepared using different metal catalysts: $Mg(N(TMS)_2)_2$, a catalyst without a chelating ligand, and $(BDI)MgN(TMS)_2$ with a chelating ligand and reacted with $Bu_4NBH_4$. With $Mg(N(TMS)_2)_2$, both PDB-PLA and BAC-PLA resulted from the reaction indicating that with this catalyst polymerization initiated at both the 2'-OH and the 7-OH of Ptxl. When $(BDI)MgN(TMS)_2$ was used, the amount of BAC-PLA derived was significantly reduced indicating polymerization of LA was with this catalyst preferentially initiated at the 2'-OH of Ptxl.

Although $(BDI)MgN(TMS)_2$ gave significantly improved site-specific control in the metal/Ptxl initiated polymerization, the resulting Ptxl-PLAs typically have fairly broad MWD (e.g., Ptxl-$LA_{200}$ $M_w/M_n$=1.47). This observation was attributed to fast propagation relative to initiation for polymerization initiated by Mg catalysts. (Chamberlain et al., 2001 supra). The catalyst $(BDI)ZnN(TMS)_2$, has a chelating ligand identical to that of $(BDI)MgN(TMS)_2$, but is less reactive compared to its Mg analogue even though it gives significantly improved polymerization of LA. When $(BDI)ZnN(TMS)_2$ was used in Ptxl-initiated LA polymerization with M/I=200. The resulting Ptxl-LA200 had an extremely narrow PDI ($M_w/M_n$=1.02) and the MW $M_n$ (obtained)=28, 100 kDa; compared to $M_n$ (expected)=29, 700 kDa). HPLC analysis of Ptxl-$LA_5$ that was prepared with $(BDI)ZnN(TMS)_2$ and then treated with $Bu_4NBH_4$ as described above demonstrated that initiation and polymerization was exclusively at the 2'-OH of Ptxl6

Drug-initiated polymerization method can be applied to the preparation of NCs of other hydroxyl-containing therapeutic agents, as well as to drugs containing one or more thiol groups. For instance, docetaxel(Dtxl)-LA10 and camptothecin(CPT)-LA10 NCs with very high drug loading (35.9 wt % and 19.5 wt %, respectively), more than 95% loading efficiencies and sub-100 nm sizes are readily prepared using this metal/drug complex initiated LA polymerization followed by nanoprecipitation (Table 1). CPT differs from both Ptxl and Dtxl as it has no intrinsic ester bond. It thus was quantitatively recovered from CPT-PLA NC after being treated with NaOH. The CPT separated from the hydrolysis mixture of CPT-PLA in PBS and collected on a preparative HPLC showed a 1H NMR spectrum identical to that of the authentic CPT. This study further demonstrated that the chemical structures of the incorporated drugs remain unchanged under the mild polymerization and nanoprecipitation processes. The incorporated drugs in NCs can be released to their original forms.

Like Ptxl-LA NCs, Dtxl-LA NCs, Doxo-LA and CPT-PLA NCs showed no burst release effects in PBS. The toxicity-drug loading correlations of both Dtxl-PLA and CPT-PLA NCs are similar to that of Ptxl-PLA NCs (FIGS. 7A-D).

The method of this invention allows preparation of polymer-drug conjugated NPs (NCs) that have very high drug loadings (up to 35%), nearly quantitative loading efficiencies, controlled release profiles without burst release effects, and narrow particle distributions. Safe, nutrient metals are involved in this formation; and organic chelating ligand can be readily removed via solvent-extraction. Additionally it takes only a few hours to prepare gram-scale, high-loading, salt-stable NCs. Drug release profiles can potentially be further controlled through the use of different cyclic ester monomers, as discussed above, for preparing NCs.

Preparation of Ptxl-PLA NC:

$(BDI)MgN(SiMe_3)_2$ (6.2 mg, 0.01 mmol) and Ptxl (8.5 mg, 0.01 mmol) were mixed in 0.5 mL anhydrous THF. DL-Lactide (144 mg, 1 mmol) in 2 mL anhydrous THF was added dropwise. After LA was completely consumed (monitored by FT-IR or 1H NMR), the polymerization solution was precipitated in ethyl ether (25 mL) to give Ptxl-$LA_{100}$ conjugate. Polymerization using $(BDI)ZnN(SiMe_3)_2$ or $Mg(N(SiMe_3)_2)_2$ were similarly performed. An acetone or DMF solution of Ptxl-$LA_{100}$ (100 µL, 10 mg/mL) was precipitated dropwise to vigorously stirred nanopure water (2 mL). PLGA-mPEG5k (MW=18,300 g/mol, 5 mg/mL in DMF, 100 µL) or mPEG5k (5 mg/mL in DMF, 100 µL) was dropwise added to NCs.

Characterization and Evaluation of Ptxl-PLA NC: NC sizes were characterized by a ZetaPALS dynamic light scattering detector (Brookhaven Instruments, Holtsville, N.Y., USA) or by SEM. The resulting NCs were purified by ultrafiltration; their in vitro toxicities were then evaluated using MTT assay in PC-3 cells (24 hr incubation at 37 C). To determine the release kinetics of Ptxl-PLA, a PBS solution of NCs was equally divided into several portions and then incubated at 37 C. At scheduled time, the release study was terminated. DMF solution was added to dissolve all precipitation. All the samples were then dried, re-dissolved in DCM and reacted with Bu$_4$NBH$_4$ for 1.5 hours. A drop of acetic acid was added into the solution. The solution was stirred for 20 min before the solvent was evaporated. The residual solid was reconstituted in acetonitrile for RP HPLC analysis (Curosil, 250×4.6 mm, 5µ; Phenomenex, Torrence, Calif., USA).

Figure 8:
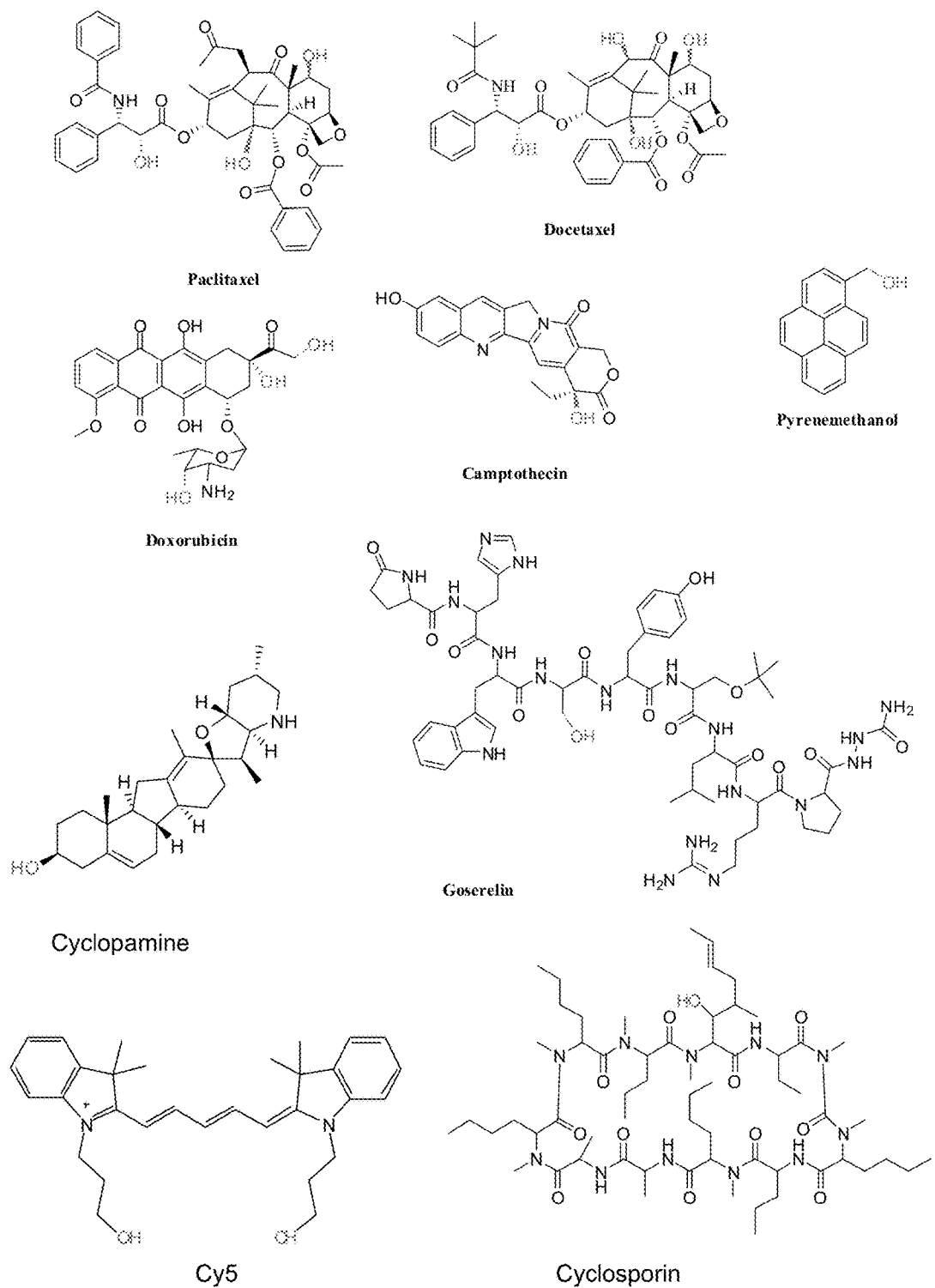
FIG. 8 provides the chemical formulas for several drugs or other chemical species (e.g., Cy5 reported dye) which have been incorporated into NCs employing the methods herein.

We have demonstrated that conjugate formation using the strategy illustrated in FIG. 2A and FIG. 2B for several different small molecules and for a peptide. The structures of these molecules are shown in FIG. 8. Representative nano-conjugate data are shown in Table 1. Exemplary detailed PLA-drug polymerization conditions are provided below. Nanoparticle formation, characterization, and release evaluation were carried out similarly to those methods used for PLA-paclitaxel nanoparticles.

Example 2

Polylactide-Doxorubicin Polymer (Doxo-PLA)

The catalyst (BDI)MgN(TMS)$_2$ and D,L-lactide were treated as in Ptxl-PLA polymerization. The polymerization was conducted in a glove box. All the reaction vessels were covered with aluminum foil and the box light was turned off. First, doxorubicin was dissolved in DMF and stirred for 10 min, until it completely dissolved. (BDI)MgN(SiMe$_3$)$_2$ was then added to and dissolved in THF. The doxorubicin and (BDI)MgN(SiMe$_3$)$_2$ solutions were mixed for 15-20 min, and the solution changed color from orange red to purple. On HPLC analysis, the peak associated with doxorubicin shifted, indicating that a complex of (BDI)MgN(SiMe$_3$)$_2$ and doxorubicin was formed. The UV detector was at 450 nm. D,L-lactide was dissolved in THF and added dropwise into the mixture of doxorubicin and (BDI)MgN(SiMe$_3$)$_2$ with rapid stirring. The reaction process was monitored by HPLC until all of the doxorubicin was gone. The UV spectrum of Doxo-LA exhibited an absorption at 325-400 nm, different from the absorption of doxorubicin at 400-500 nm. Nanoparticles were formed by nanoprecipitation similarly to Ptxl-PLA nanoparticles.

Example 3

Dtxl-PLA using 1, 5, 7-Triazabicyclo[4.4.0]dec-5-ene (TBD) or BDI-Mg-N(TMS)$_2$

The TBD or BDI-Mg-N(TMS)$_2$ catalyst was mixed with docetaxel and the lactide was added to the mixture of catalyst and initiator. For example, docetaxel and TBD were dissolved in THF solution and stirred for 5-10 min. (In HPLC, the peak of docetaxel shifted, indicating the TBD formed complex with docetaxel). D,L-Lactide was dissolved in THF solution and added dropwise into the mixture of docetaxel and TBD. The reaction was similar to that of paclitaxel-PLA, monitored by FTIR and HPLC. Polymerization initiated by docetaxel-Mg(II) complex was carried out in the same way as described above for paclitaxel. Nanoparticles were formed similarly to Ptxl-LA nanoparticles.

Example 4

PLA-Pyrenemethoxy Polymerization

Pyrenemethanol (TCI America) was purified by dissolving in THF with CaH2 and stirring overnight, filtered and vacuum dried and stored in glove box freezer. The pyrenemethanol was mixed with the LA in BDI-Mg-N(TMS)$_2$. The ratio of monomer to initiator (Pyr) was selected. After 24 hours the reaction was stopped and purified by washing with methanol and ether for three times. NMR confirmed the PLA copolymer formation conjugated with pyrenemethanol. Nanoparticles were formed similarly as Ptxl-PLA nanoparticles.

Examples 5

PLA-LHRH Polymerization

Goserelin was obtained from Bachem and stored in a freezer. (BDI)MgN(SiMe$_3$)$_2$ and D,L-Lactide were treated as described above for Ptxl-PLA polymerization. The polymerization was conducted in a glove box. Goserelin was dissolved in DMF solution with stirring for 10 min. (BDI) MgN(SiMe$_3$)$_2$ was dissolved in THF solution. The goserelin and (BDI)MgN(SiMe$_3$)$_2$ solutions were mixed for 30 min with stirring. D,L-Lactide was dissolved in THF and added into the mixture. The ratio of lactide to goserelin was selected. During polymerization, the solution may become cloudy indicating precipitation of some species. If this occurs, more DMSO can be added to keep the components and products in solution. The conversion of goserelin was detected by HPLC. The conversion observed was however less than 95%. Nanoparticles were formed from the groserelin-conjugates as described for Ptxl-PLA nanoparticles.

Example 6

Zn, Ca and Fe Catalysts, and Organocatalysts

Mg(II) complexes gave fast polymerization. However, in some instances Mg(II) may give significantly faster propagation than initiation which is undesirable for carrying out a living polymerization. Coates has demonstrated that certain Zn catalysts facilitate fast initiation and relatively slow chain propagation and Zn-mediated lactide polymerization can result in polymers with narrow polydispersity.[19] Therefore, (BDI)Zn-(docetaxel) and (BDI)Zn-(doxorubicin) are useful as initiators in the methods herein. Other catalysts useful for these methods include those of Ca and Fe.[16] Mg, Zn, Ca, and Fe are elements found in human body, therefore they have should better safety profile than other active catalysts such as Al and Sn. Exemplary catalyst include, among others,

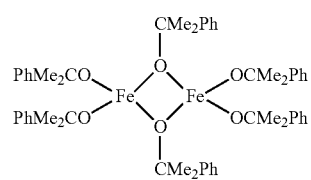

10

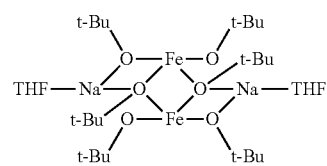

11

-continued

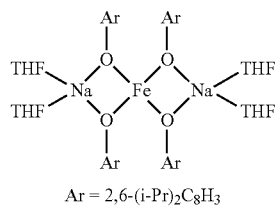

Ar = 2,6-(i-Pr)₂C₆H₃

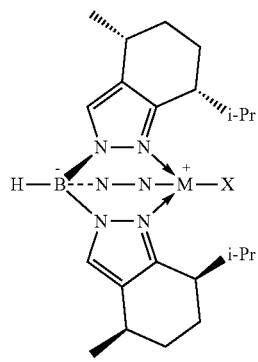

22a: M = Zn, X = OSiPh₃
22b: M = Mg, X = OPh

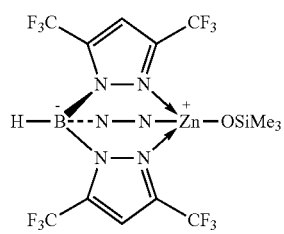

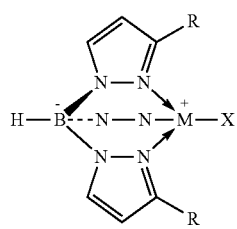

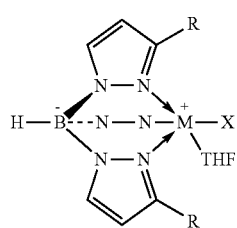

M = Mg, Ca, Zn
X = OEt, OPh, O[2,6-(i-Pr)₂C₆H₃], OSiMe₃, N(SiMe₃)₂
R = t-Bu, i-Pr

-continued

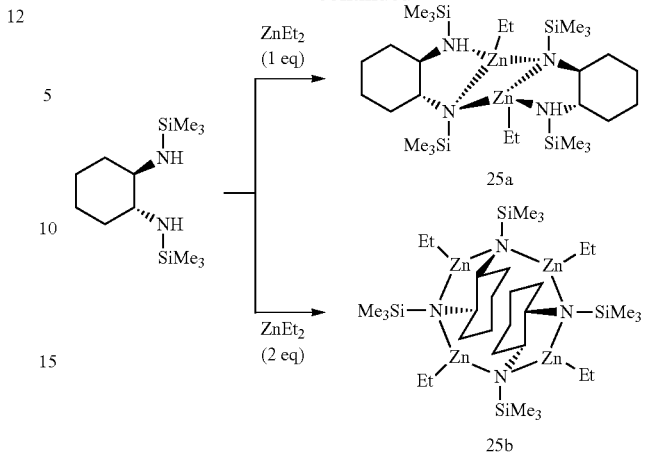

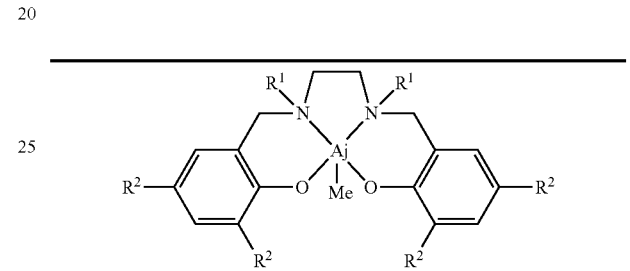

| complex | R¹ | R² |
|---------|-----|------|
| 48a | Me | H |
| 48b | Me | Me |
| 48c | Me | t-Bu |
| 48d | Me | Cl |
| 48e | CH₂Ph | H |
| 48f | CH₂Ph | Me |
| 48g | CH₂Ph | t-Bu |
| 48h | CH₂Ph | Cl |

L₁ZnN(SiMe₃)₂ (29a)
L₁ZnN(i-Pr)₂ (29b)
(L₁ZnOi-Pr)₂ (29c)
L₁Zn(OSiPh₂)(THF) (29d)
L₁ZnOt-Bu (29e)
L₁ZnOCHMeCO₂Me (29f)
(L₁ZnOAc)₂ (29g)
L₁ZnEt (29h)
L₁SnOi-Pr (30)
L₁Mg[N(i-Pr)₂](THF) (31a)
(L₁MgOi-Pr)₂ (31b)
L₁Mg(Ot-Bu)(THF) (31c)
L₁Ca[N(SiMe₃)₂](THF) (32)
L₂FeOt-Bu (33), where

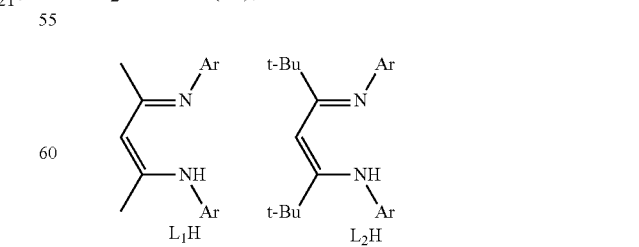

Ar = 2,6-(i-Pr)₂C₆H₃ or Ar=2,6-(Ethyl)₂C₆H₃.

Example 7

Release Studies

Pyrenemethanol-PLA Release Study

Free pyrenemethanol was used to calibrate the concentration-HPLC peak area (or intensity) curve. The nanoparticle was formed in acetonitrile (10 mg/ml)-water (1/10) system and washed by DI water three times to remove non-covalently bound small molecules. At day 0, the PBS 1X-NP solutions were prepared in several vials and incubate at 37 C. Two vials were used in an experiment. The content of one vial was centrifuged at 4000 rpm for 30 min to spin down all the NPs and the concentration of pyrenemethanol concentration in the supernatant was measured. 1N NaOH solution was added to the other vial at 37 C for 30-90 min to degrade all the NPs and the total concentration of pyrenemethanol (100%) was measured. (Before injection into the HPLC, the pH value of the solution was adjusted to 7 using acetic acid). At a selected time point, a vial is taken from the 37 C incubator, NPs are spun down to get the supernatant and prepare to 1/1 PBS-acetonitrile solution and injected into HPLC. The integrated peak and intensity was documented and compared with measurement of total 100% pyrenemethanol concentration in the nanoparticles to determine the release profile. The HPLC detector monitored for absorption at 227 nm and 265 nm. The mobile phase used is 50/50 acetonitrile/DI water with 0.05% TFA.

Docetaxel-PLA Release Study

Free Docetaxel was used to calibrate a standard curve in HPLC analysis. The PLA-docetaxel nanoparticles were well dispersed in 1×PBS solution and extracted with 1-octanol. The 1-octanol extract was directly injected into the HPLC. The analysis condition used were the same as used for PLA-pyrenemethanol, and the detector monitored at 227 nm and 265 nm. The percentage of release is determined by the comparison of the amount of docetaxel in 100% incorporation polymer at the same HPLC injection concentration.

Example 8

Dendritic Nanoconjugates in 2-20 nm Range

Because drug release kinetics are directly correlated to nanoparticle surface area, further miniaturization of nanoparticles will result in even faster drug lease. In addition, small nanoparticles can have dramatically different properties for drug delivery and other applications compared to larger particles. For example, small nanoparticles should have different cell uptake characteristics. For relatively large particle size (~100 nm), particles can be endocytosed. But when the NP is in ~10 nm range, direct particle penetration or entry through solution pinocytosis (cell drinking) is possible. Micellation of block copolymers typically results in particles larger than the 10 nm range.

To prepare smaller size nanoparticles, dendritic polymer or oligomer conjugates can be used. Such conjugates are formed by polymerization AB2 type cyclic monomers, such as hydroxyl lactides:

Formula H

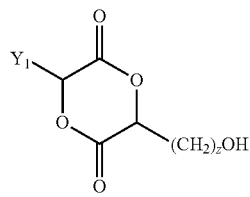

where z is 1-6 and $Y_1$ is as defined above. In specific embodiments $Y_1$ is H.

Figure 9:
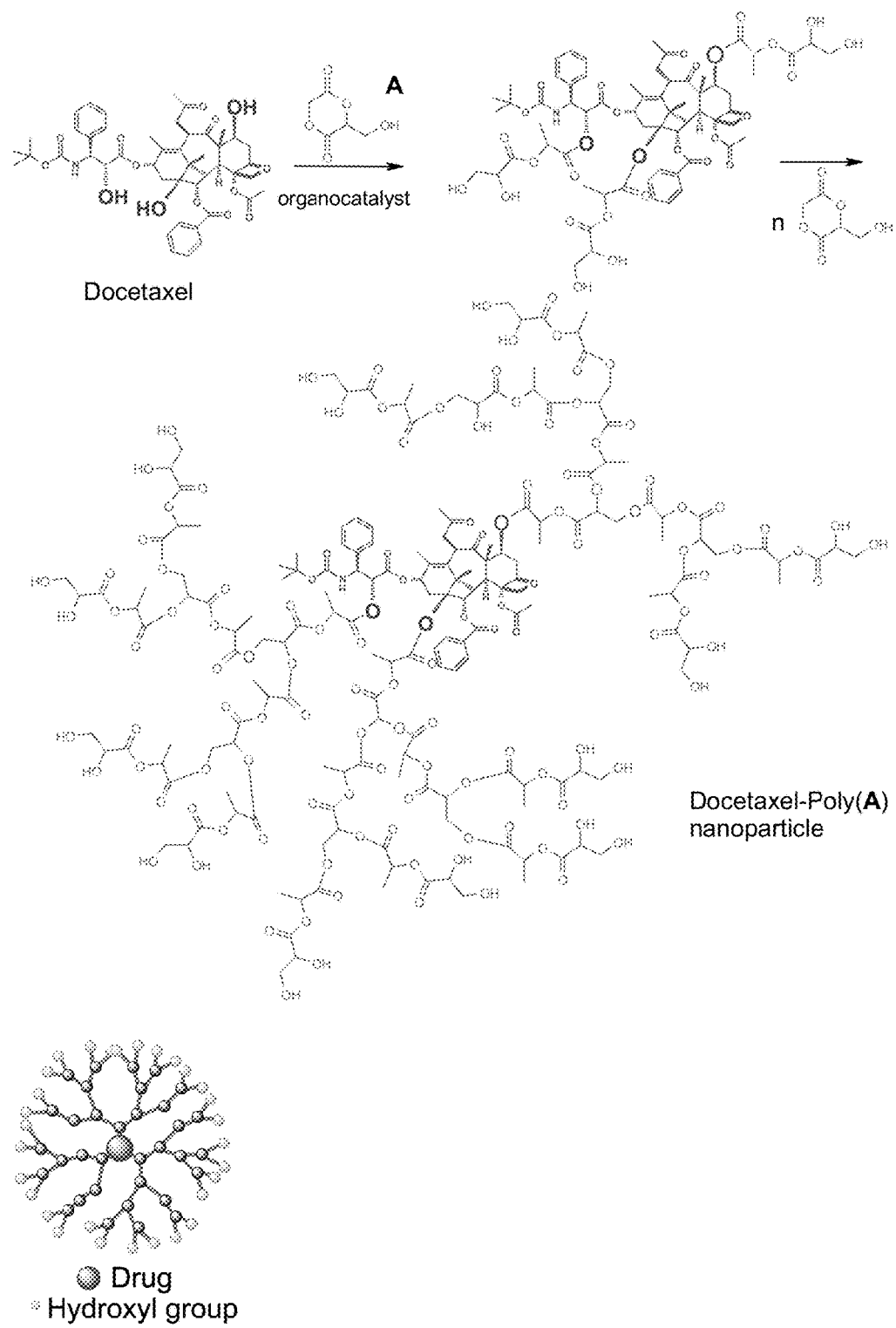
FIG. 9 is a schematic illustration of a method for preparation of dendritic nanoparticles, which are believed to be unimolecular dendritic particles containing one therapeutic in each nanoparticle. The polymerization method is similar to that described. These dendritic particles give <20 nm particle size, a range unachievable using other strategy.

For example, the AB2 monomer of Formula H where z is 1 and $Y_1$ is H can be used. This monomer is synthesized as illustrated in Scheme 1 below. Polymerization of the hydroxyl lactide molecule in the presence of a drug having at least one hydroxyl or thiol group results in formation of a conjugate having a dendritic or hyperbranched structure as illustrated in FIG. 9.

In another specific embodiment, in which the drug or other chemical species has one hydroxyl group, a single attached polymer can form a hyperbranched structure around the drug molecule. In a specific embodiment, in which the drug or other chemical species has two or more hydroxyl groups, multiple attached polymers can form a hyperbranched structure around the drug molecule. This embodiment is exemplified in FIG. 9. It will be appreciated, that not all hydroxyl groups in the drug or other species, will have the same reactivity for initiation of polymerization and attachment of the polymer or oligomer. Thus, for a given drug or other chemical species, the polymer or oligomer may be formed selectively at fewer than all hydroxyl groups. Also a given population of polymer/oligomer conjugates may be heterogeneous with respect to the number of polymers/oligomers attached to each drug or other chemical species, i.e., it may be that not all of the conjugates will have the same number of attached polymer/oligomers. The formation of sufficient hyperbranched structure results in the formation of a unimolecular dendritic nanoparticle. This method employing a cyclic AB2 type monomer can result in the formation of small particle size nanoparticles (20 nm or less) containing a selected drug. The resulting nanoparticles are water soluble as the hyperbranched polyester structure has many peripheral hydroxyl groups.

Scheme 1

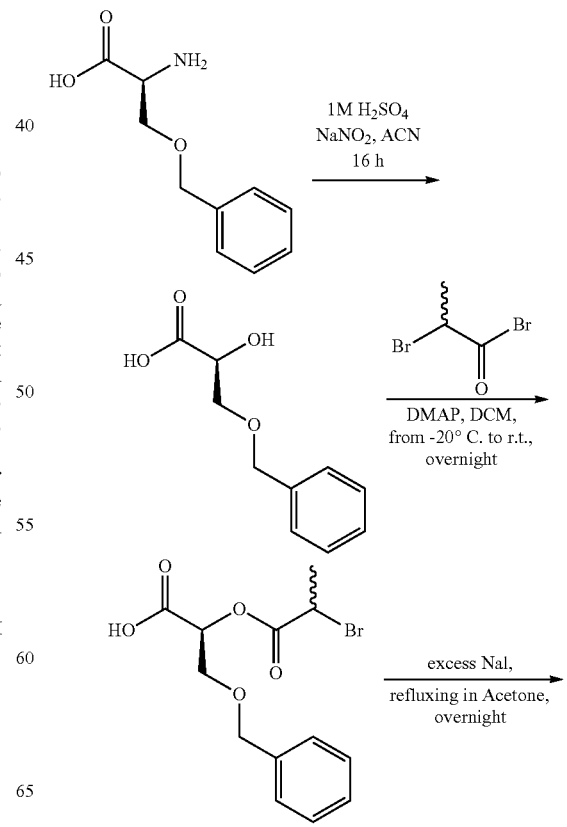

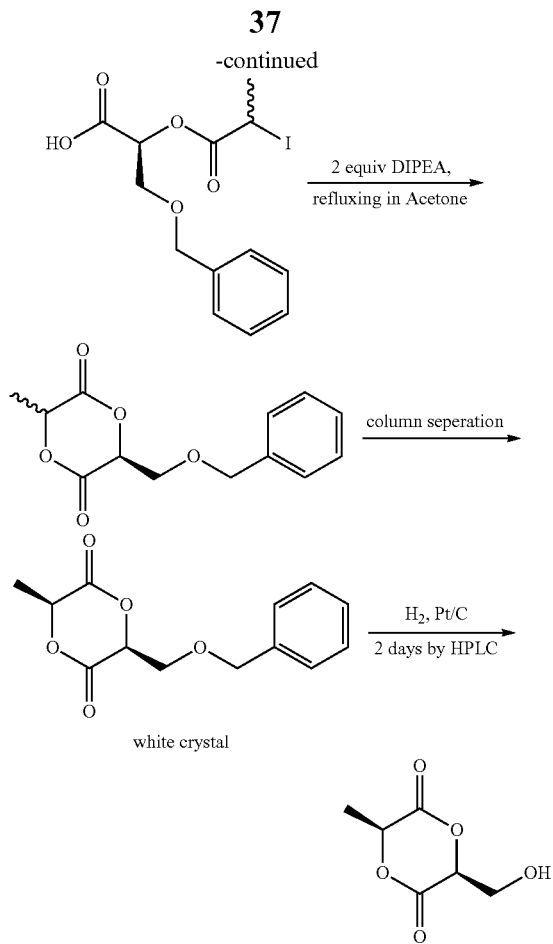

In the synthesis of Scheme 1, H-Ser(Z)-OH (30.0 mg, 154 mmol) was dissolved in 1M sulfuric acid 400 ml and acetonitrile 400 ml. NaNO$_2$ (21.7 g 313 mmol) was dissolved in 150 ml water and added dropwise into the reaction flask over 30 min. The reaction was stirred for 18-24 hours under nitrogen protection. The solution was extracted with dichloromethane and ethyl acetate 500 ml (3 times). The combined organic layers were dried with magnesium sulfate, filtered, and concentrated in vacuo. The resulting product (25.4 g, 129 mmol) was dissolved in dichlormethane (300 ml) with 17.9 ml triethylamine and added dropwise (over 30 minutes) into 2-bromopropionyl bromide (13.5 ml 129 mmol) and DMAP (1.58 g, 129 mmol) in 150 ml dichloromethane solution in an ice cold bath. The reaction was thereafter stirred for 18-24 hours under nitrogen. The mixture was precipitated using ether and the remaining solution was filtered. The combined organic solution was evaporated to give a light yellow oil (product of second step).

Sodium iodine (18.59 g, 1.24 mol, 10 equivalents) was added into 500 ml acetone solution containing the product of the second step (4.11 g, 12.4 mmol) and the mixture was refluxed overnight. Temperature was controlled to 55-60 C under nitrogen. The reaction was stopped and cooled down the next day. Solvent (acetone) was filtered using celite and the acetone was evaporated. The resulting brown oil was redissolved in acetone and extracted with Na$_2$S$_2$O$_3$ 2M (300 ml) (3 times) to give a yellow solution which was dried with MgSO$_4$. Finally the solvent was evaporated to give a crude product (of step three) which was used without further purification.

A solution of this product (4.53 g 12.1 mmol) in 100 ml DCM was added dropwise to refluxing DIEA (4.6 ml, 27.7 mmol) in 1000 ml acetone over 8 hours. The temperature was controlled at 70° C. HPLC confirmed that the reaction was complete. The diastereomers were separated on a silica gel column by eluting with chloroform and methyl tert butyl ether (1/1). The solvent was evaporated and the solid was redissolved in methyl tert butyl ether, and then excess hexane was added to the solution to precipitate out a white solid.

The white solid (1.5 mmol, 375.0 mg) was dissolved in methanol (1.5 m) and the Cbz group was deprotected by H$_2$ with 10% Pd/C catalyst (40 mg). After two days the solution was evaporated to give a white solid. NMR and El-MS confirmed the structure.

The polymerization of the hydroxyl substituted cyclic monomer (1.0 mmol, 160 mg) is conducted in a glove box. The monomer is dissolved in 500 ul DMF solution. (BDI) MgN(SiMe$_3$)$_2$ (0.03 mmol, 18.0 mg) is dissolved in 1 ml THF and mixed with docetaxel (0.01 mmol, 8.1 mg) in THF solution for 10-30 min. The monomer solution is very slowly added into the mixture over 10 min. The reaction is monitored by HPLC at 227 nm and 265 nm. After finishing the reaction, the polymer is purified by reverse-phase semi-preparative HPLC using a SEC column. The polymer forms micelles in water solution and the size of the particles formed is in the range from 5-30 nm, as characterized by AFM and dynamic light scattering measurement.

Example 9

Design of Nanoconjugates in 20-60 nm Range

It is a challenge to make nanoparticles smaller than 60 nm, particularly by precipitating hydrophobic PLA or Dtxl-PLA. Micellation can, however, be used to make nanoparticles with precisely controlled sizes in a range of 20-60 nm. PEG is conjugated to the terminal —OH group of Dtxl-LA. The conjugation of PEG can be performed after the polymerization conjugation. Alternatively, a single reaction step can be employed. After each polymerization, the terminal hydroxyl group is reactive to capping groups like isocyanate. PEG-isocyanate, for example, is used as a capping agent to cap the terminal hydroxyl groups of drug-PLA conjugate. PEG-isocyanate is readily prepared by reacting PEG-N H$_2$ with triphosgene. Reaction of PEG-isocyanate with Dtxl-LA-OH is fast, and results in Dtxl-LA-urethane linker-PEG in quantitative yield. After purifying the conjugated polymer through an SEC column, the purified conjugated polymer is used to formulate micelles. When PEG with higher average MW is used, micelles with small particle size (20 nm-60 nm) can be readily generated. The use of PEG-poly(aspartic acid)-drug conjugates to form copolymer micelles has been extensively studied by Kataoka,[20] Kwon[21,22] and the inventors.[23,24]

In a specific example, mPEG5k-NH$_2$ 500 mg (0.1 mmol) was dissolved in dichloromethane (10 ml) with stirring. Triphosgene 269.8 mg (1 mmol) was added to the solution and the reaction mixture was refluxed at 50-60 C for at least 2 hours. The reaction was monitored by FTIR, where the isocyanate peak appears at 2250 cm$^{-1}$. The yield is calculated by the titration of the mPEG5k-NCO with the quantified pyrenemethanol to determine the concentration of the mPEG5k-NCO in the solution. After the reaction is complete, the solvent is evaporated and the polymer is washed with hexane and cold ether (3 times). Unreacted mPEG5k-NH$_2$ is separated from the product by a size exclusion column using THF or acetonitrile/hexane as eluent. The product is dried in vacuuo and stored under a nitrogen atmosphere in the freezer.

Example 10

Double Emulsion Technique Design of Nanoparticles (100-600 Nm), Exemplified with Dtxl-LA Conjugates Drug encapsulated microparticles are prepared using a water-in-oil-in-water (W/O/W) solvent evaporation procedure. In brief, 50 microliter of water was emulsified in a 1 mL solution of the polymer conjugate (Dtxl-LA) (50 mg) in dichloromethane using a probe sonicator (Sonic & Materials Inc, Danbury, Conn., USA) at 10 W for 15-30 s. The emulsion was then poured into 50 mL of aqueous PVA (1%) or sodium cholate solution (1% w/v) and the mixture was homogenized for 1 min (8000 rpm). The resulting emulsion was poured into 150 mL of aqueous PVA or sodium cholate solution (0.3% w/v) with gentle stirring, after which organic solvent was evaporated by stirring at RT for 2 h or rapidly removed using a rotary evaporator. Finally, the nanoparticles were isolated by centrifugation at 6000 rpm for 30 min, washed with distilled water, and preserved at −15° C. in an emulsion form in distilled water (6 mL). Alternatively, the nanoparticles can be lyophilized to obtain a powder.

Example 11

Double Emulsion Method for Preparation of Microparticles (600 nm-100 µm)

Drug encapsulated microparticles are prepared using the water-in-oil-in-water (W/O/W) solvent evaporation procedure (double emulsion method) employed elsewhere. In brief, 50 microL of water is emulsified in a 1 mL solution of the polymer conjugate (Doxo-LA) (50 mg) in dichloromethane using a probe sonicator (Sonic & Materials Inc, Danbury, Conn., USA) at 10 W for 15-30 s. The emulsion is then poured into 50 mL of aqueous PVA (1%) or sodium cholate solution (1% w/v) and the mixture is homogenized for 1 min at a speed of 500-8000 rpm. The resulting emulsion is poured into 150 mL of aqueous PVA or sodium cholate solution (0.3% w/v) with gentle stirring, after which organic solvent is evaporated by stirring at room temperature for 2 h or is rapidly removed using a rotary evaporator. Finally, the nanoparticles are isolated by centrifugation at 6000 rpm for 30 min, washed with distilled water, and preserved at −15° C. in emulsion form in distilled water (6 mL) or are lyophilized to obtain a powder.

Example 12

Surface Functionalization Using Herceptin

Trastuzumab (Herceptin) is dissolved at 1 mg/ml in phosphate buffer (pH=8.0). 2-iminothiolate (5.7 mg) is dissolved in 5 ml phosphate buffer at pH 8.0. The 2-iminothiolate solution (8.04 microL) is mixed with 1 ml Trastuzumab solution for 6 hours at 20° C. The resulting thiolated antibody can be purified using a Dextran Desalting SEC column with phosphate buffer as eluent and detecting at 280 nm. The antibody solution is further concentrated using a Microcon 30000 microconcentrator. The thiol group concentration in the antibody solution can be determined using Ellman reagent. The antibody solution 250 ul is mixed at room temperature with 6.25 ul 4 mg/ml Ellman reagent (in phosphate buffer pH=8.0) for 15 min, and detected by the UV spectrometer at 412 nm. The number of thiol groups is calculated relative to an L-cysteine standard solution.

MAL-PEG5k-isocyanate (where, MAL is a malimide group) is conjugated to Doxo-PLA at room temperature for 8 hours and the polymer is purified on an SEC column. The polymer is dissolved in acetone at 10 mg/ml concentration and added dropwise under vigorous stirring into water with the volume ratio of acetone:water=1/20. The coupling reaction of thiol of the antibody and the malimide of the polymer is then conducted in nanopure water solution at room temperature. The reaction is allowed to continue for at least 12 hours. The SEC column is used to detect unbounded thiolated antibody in the water phase. After conjugation, the efficiency is determined by compared the peak area of thiolated antibody from the SEC column before reaction at the same concentration.

There is an alternative method for incorporation of thiolated antibody. The PLGA-PEG-MAL (poly(lactic-glycolic acid)-poly(ethylene glycol) copolymer with a terminal malimide group) or PLA-PEG-MAL (poly(lactic acid)-poly (ethylene glycol) copolymer with a terminal malimide group) can either be purchased or made by known methods. First the Doxo-LA is dissolved in acetone and the material is nanoprecipitated to form nanoparticles. Then an acetone solution of PLGA-PEG-MAL or PLA-PEG-MAL is added dropwise to the nanoparticle. Use of this method keeps the particle distribution unchanged. The further conjugation between the malamide and thiol group of the antibody is performed as described above.

After conjugation, the nanoparticle is surface-modified with the herceptin. The function of the antibody can be tested. The nanoparticles are incublated with MCF-7 and SK-BR-3 cells for 3 days after which western blotting analysis is performed. The SK-BR-3 cell that express HER 2 and MCF 7 cells are used as a negative control.

Example 13

Preparation of Cyclopamine (CA) NCs

The preparation of CA-LA$_{100}$ nanoconjugates involved two steps. The first step was to conjugate CA with PLA polymer. Briefly, in the glove box, cyclopamine (4.11 mg, 0.01 mmol) was dissolved in 1.0 mL THF solution. (BDI) MgN(SiMe$_3$)$_2$ (6.0 mg, 0.01 mmol) was mixed with CA for 5-15 min. DL-Lactide (144 mg, 1.0 mmol) in 1 mL THF solution was added dropwise to the mixture of CA and (BDI)MgN(SiMe$_3$)$_2$ with vigorous stirring. FTIR was used to calculate the conversion of Lactide. The reaction finished overnight and CA-LA$_{100}$ conjugated polymer was obtained. The second step was to use the polymer solution to directly prepare NPs by the nanoprecipitation method. CA-LA$_{100}$ polymer in DMF solution was added dropwise into 20× nanopure water, a non-solvent. The resulting NPs suspension can be purified by ultrafiltration (15 min, 3000 g, Amicon Ultra, Ultracel membrane with 10,000 NMWL, Millipore, Billerica, Mass.).

Example 14

Preparation of Cyclopsporin (CP) NCs

The preparation of CP-LA-$_{100}$ nanoconjugates involved two steps. The first step was to conjugate CP with PLA polymer. Briefly, in the glove box, cyclosporine 12.02 mg (0.01 mmol) was dissolved in 1.0 mL THF solution. (BDI)MgN(SiMe$_3$)$_2$ (6.0 mg, 0.01 mmol) was mixed with CA for 5-15 min. DL-Lactide (144 mg, 1.0 mmol) in 1 mL THF solution was added dropwise to the mixture of CA and (BDI)MgN(SiMe$_3$)$_2$ with vigorous stirring. FTIR was used to calculate the conversion of Lactide. Finally the reaction finished overnight and CA-100 polymer was obtained. The second step was to use the polymer solution to directly prepare NPs by nanoprecipitation method. In general, CA-100 polymer in DMF solution was dropwise added into 20× nanopure water, a non-solvent. The resulting NPs suspension can be purified by ultrafiltration (15 min, 3000 g, Amicon Ultra, Ultracel membrane with 10,000 NMWL, Millipore, Billerica, Mass.).

Example 15

Preparation of Core-Shell Nanoconjugates (50-200 nm Range) Including Those Containing Two or More Drugs Doxo-LA$_{25}$ polymer (5 mg/mL in DMF, 100 μL) was added dropwise to 2 mL nanopure water to give Doxo-LA$_{25}$ NCs. PLGA-mPEG5k (MW=18,300 g/mol, 5 mg/mL in DMF, 100 μL) or mPEG5k (5 mg/mL in DMF, 100 μL) was then added dropwise to Doxo-25 NP. The NC that resulted are core-shell NCs where the core is Doxo-LA25 and the shell is PLGA-mPEG5k or mPEG5k.

Ptxl-LA$_{200}$ conjugate (2 mg/mL in DMF, 100 μL) was added dropwise to 2 mL nanopure water to give Ptxl-LA200 NCs. PLA-PEG3k (MW=17,500 g/mol, 2 mg/mL in DMF) was then sequentially added into Ptxl-LA200 NCs solution under vigorous stirring. The resulting NCs are core-shell NCs.

Analogous methods can be employed with drug-polymer conjugate prepared by the methods herein to form analogous nanoconjugates with core-shell structure.

Dtxl-LA$_{100}$ (core)/Doxo-LA$_{100}$ (Shell) NCs: Dtxl-LA$_{100}$ in DMF (10 mg/mL, 100 μL) was added dropwise into 2 mL nanopure water to form nanoparticles (NCs) and thereafter Doxo-LA100 in DMF(10 mg/mL, 100 μL) was further added into the nanoparticle solution with vigorous stirring (3000 rpm) at 50 μL/min rate. The resulting NCs are dual drug core-shell NCs illustrated in FIG. 10A. In this figure the shift in particle size from about 80 to about 100 nm is illustrated.

Ptxl-LA$_{100}$/CPT-LA$_{100}$: Ptxl-100 in DMF (10 mg/mL, 100 μL) was added dropwise into 2 mL nanopure water and the CPT-100 in DMF (10 mg/mL, 100 μL) was further added into the nanoparticle solution with vigorous stirring (3000 rpm) at 50 μL/min rate.

These methods can be employed to prepare NCs containing multiple drugs employing any drug-polymer conjugate made by the methods herein. The methods can also be employed to prepare NCs where the core and shell are made from different polymer conjugates with the same drug e.g. Ptxl-LA$_{200}$/Ptxl-LA$_{100}$, or Ptxl-LA$_{100}$/Ptxl-LA$_{200}$. In the above methods the relative amounts of polymer conjugate can be varied as desired to obtain particle so desired size and properties.

FIG. 10B is a graph showing the change in particle size of NCs on addition of different polymer conjugates to the NC to form core-shell NCs.

Particle sizes for FIGS. 10A and B were analyzed by dynamic light scattering. More specifically, particle sizes were detected by a ZetaPALS dynamic light-scattering (DLS) (15 mW laser, incident beam=676 nm; Brookhaven Instruments, Holtsville, N.Y.).

Example 16

Cytotoxicity Test for NCs

PC-3 cells were plated in a 96-well plate for 24 h (10,000 cells per well). On the day of experiments, cells were washed with prewarmed PBS and different concentration of fresh prepared NCs (prepared in 1×PBS) was added. The control cells were incubated with medium. The cells were incubated for a total of 24 hours in the incubator at the 5% $CO_2$ atmosphere. After that, the medium was removed and reconstitute with MTT solution and OptiMEM medium for a further incubation of 3 hours. The resulting crystals were dissolved and final cell viability was assessed colorimetrically by microplate reader at 655 nm. The results of certain cyctoxicity studies are shown in FIGS. 7A-D for NCs formed with Ptxl, Dtxl, CPT, and Doxo with varying M/I ratios compared to free drug as shown in the figure.

Analogous MTT cytotoxicity tests were performed using NC carrying multiple drugs in human prostate cancer cells, PC-3 cells, with 72 hours of incubation. Relative toxicities of a series of NC as measured by $IC_{50}$ is reported in Table 3.

TABLE 3

| MTT Cytotoxicity for Multi-Drug Loaded NCs | |
| --- | --- |
| NC | $IC_{50}$ |
| Ptxl-LA$_{25}$ | 837.22 ± 29.81 |
| Ptxl-LA$_{25}$/CA-LA$_{25}$ | 622.14 ± 14.61 |
| Ptxl-LA$_{25}$/CA-LA$_{10}$ | 168.01 ± 10.79 |
| Doxo-LA$_{25}$ | 286.68 ± 5.65 |
| Doxo-LA$_{25}$/CA-LA$_{25}$ | 240.16 ± 18.36 |
| Doxo-LA$_{25}$/CA-LA$_{10}$ | 84.89 ± 7.14 |

As shown in the results of Table 3, the dual drug NC's combining the taxane (paclitaxel) and cyclopamine or the anthracycline antibiotic (doxorubicin) and cyclopamine exhibit synergistic effect against the prostate cancer cells. With being bound to any particular theory of activity, it is believed that inhibition of Shh by cyclopamine substantially improved the efficacy of the taxane and anthracycline antibiotic against cancer cells.

Example 17

Figure 11A:
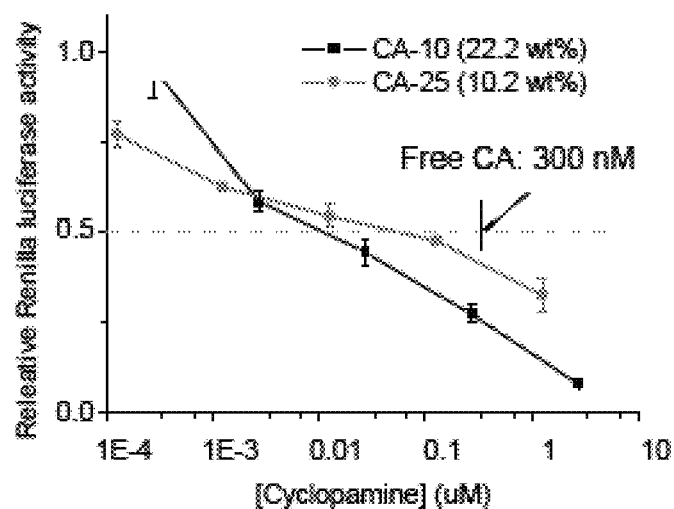
FIGS. 11A and 11B provide the results of luciferase assays of NC containing cylcopamine added to Shh-Light 2 cells bearing luciferase-encoded Gli-1 gene.
Figure 11B:
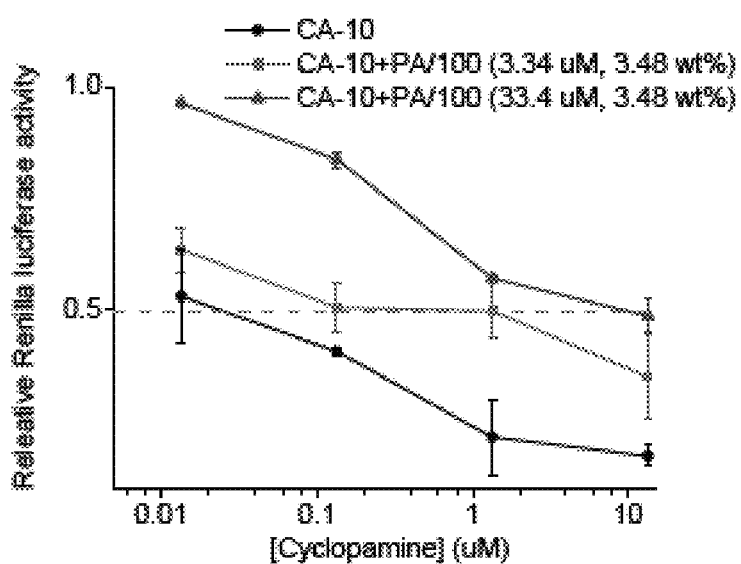

Inhibition of the Hedgehog Pathway Using NCs Containing Cyclopamine Assessed Using a Luciferase Assay Shh-LIGHT2 cells, which stably incorporated Gli-dependent firefly luciferase and constitutive *Renilla luciferase* reporters, were cultured to confluency in 96-well plates and then treated with (1) various concentrations of cyclopamine carried in PLA-cyclopamine NCs (e.g., CA-LA$_{10}$ NCs or CA-LA$_{25}$ NCs) in DMEM containing 0.5% bovine calf serum with or without (2) PLA-purmorphamine NEs. FIG. 11A is a graph of relative *Renilla Luciferase* activity as a function of cyclproamine concentration (microM). The treated cells were then cultured for 36 h under standard conditions, and firefly and *Renilla luciferase* activities were determined using a dual luciferase kit (Promega) according to the manufacturer's protocols.

Example 18

Effect of Catalyst on Structure of Conjugates

As described above in Example 1, in cases in which the drug or other chemical species carried more than one functional group that can function for initiation of polymerization with a catalyst, the structure or nature of the catalyst can affect which of the functional groups is involved in the polymerization and to the site or sites in the drug (or other chemical species) the growing polymer attaches. FIG. 12 shows the effect of use of different catalysts on the molecular weight and polydispersity (PDI) of drug-polymer conjugates made by the methods herein. In a specific case, the figure shows the results of using different catalysts on conjugate formation with pacitaxel using LA/Ptxl/catalyst molar ratio of 200/1/1 to prepare Pxtl-LA200 of expected MW of 29,653. Ptxl formally contains three OH groups (2'-OH, 1-ON and 7-OH) that could initiate polymerization of LA. As noted above, however, it is considered less likely for steric reasons that the 1-OH would be involved in initiation which is believed to involve metal oxide formation with the OH group. It is believed that a source of polydispersity in the formation of Pxtl-LA conjugates is the formation of some portion of the conjugates with polymer attached at two sites in the molecule. As shown in the figure, the actual MW and the PDI as measured by standard Gel Permeation Chromatography of Pxtl-LA$_{200}$ conjugates varies as a function of the catalyst used. Use of Zn catalyst with bulky ligands (catalysts 4 and 5, from FIG. 12) results in conjugates with lower polydispersity. It is believed that the lower polydispersity is associated with increased selectivity for polymer attachment to one site, likely the 2'-OH site in Ptxl.

Example 19

Determination of MW and PDI of Drug-Polymer Conjugates Using Gel Permeation Chromatography Drug-polymer conjugates were prepared as described in previous examples employing the drug as the initiator (in the presence of catalyst) for polymerization of LA. Actual MW and PDI were measured using well-known methods of Gel Permeation Chromatography.

TABLE 4

GPC data of Nanoconjugates containing Ptxl, CPT, Dtxl, Doxo, CA or CP

| NC | Expected MW | Actual MW | PDI |
|---|---|---|---|
| Ptxl-LA$_{200}$ | 29653 | 28160 | 1.021 |
| Ptxl-LA$_{150}$ | 22453 | 22490 | 1.032 |
| Ptxl-LA$_{100}$ | 15253 | 14030 | 1.043 |
| Ptxl-LA$_{50}$ | 8053 | 9658 | 1.040 |
| Cpt-LA$_{200}$ | 29148 | 30440 | 1.176 |
| Cpt-LA$_{100}$ | 14748 | 20080 | 1.207 |
| Cpt-LA$_{75}$ | 11148 | 12670 | 1.173 |
| Cpt-LA$_{50}$ | 7548 | 8978 | 1.257 |
| Cy5-LA$_{300}$ | 43706 | 44550 | 1.098 |
| Cy5-LA$_{200}$ | 29306 | 30790 | 1.213 |
| CA-LA$_{150}$ | 22011 | 22620 | 1.166 |
| CA-LA$_{100}$ | 14811 | 19800 | 1.102 |
| Dtxl-LA$_{300}$ | 44006 | 51350 | 1.045 |
| Dtxl-LA$_{200}$ | 29606 | 30600 | 1.095 |
| Dtxl-LA$_{100}$ | 15206 | 20700 | 1.086 |
| Dtxl-LA$_{50}$ | 8006 | 12090 | 1.169 |
| CP-LA$_{200}$ | 30002 | 40150 | 1.161 |
| CP-LA$_{100}$ | 15602 | 31810 | 1.324 |
| CP-LA$_{50}$ | 8402 | 21440 | 1.337 |
| Doxo-LA$_{200}$ | 29343 | 40630 | 1.156 |
| Doxo-LA$_{100}$ | 14943 | 19400 | 1.253 |

The forgoing examples are illustrative and in no way are intended to limit the scope of the invention.

1. Duncan, R. The dawning era of polymer therapeutics. *Nature Reviews Drug Discovery* 2, 347-360 (2003).
2. Duncan, R. Polymer conjugates as anticancer nanomedicines. *Nature Reviews Cancer* 6, 688-701 (2006).
3. Haag, R. & Kratz, F. Polymer therapeutics: Concepts and applications. *Angewandte Chemie-International Edition* 45, 1198-1215 (2006).
4. Kim, C. J. Effects of drug solubility, drug loading, and polymer molecular weight on drug release from polyox (R) tablets. *Drug Development and Industrial Pharmacy* 24, 645-651 (1998).
5. Kataoka, K., Harada, A. & Nagasaki, Y. Block copolymer micelles for drug delivery: design, characterization and biological significance. *Advanced Drug Delivery Reviews* 47, 113-131 (2001).
6. Wagner, V., Dullaart, A., Bock, A. K. & Zweck, A. The emerging nanomedicine landscape. *Nature Biotechnology* 24, 1211-1217 (2006).
7. Gradishar, W. J. Albumin-bound paclitaxel: a next-generation taxane. *Expert Opinion on Pharmacotherapy* 7, 1041-1053 (2006).
8. Desai, N. & Soon-Shiong, P. (U.S. Pat. No. 6,506,405, US, 2003).
9. Desai, N. & Soon-Shiong, P. (U.S. Pat. No. 6,753,006, US, 2004).
10. Musumeci, T. et al. PLA/PLGA nanoparticles for sustained release of docetaxel. *International Journal of Pharmaceutics* 325, 172-179 (2006).
11. Dong, Y. C. & Feng, S. S. Methoxy poly(ethylene glycol)-poly(lactide) (MPEG-PLA) nanoparticles for controlled delivery of anticancer drugs. *Biomaterials* 25, 2843-2849 (2004).
12. Avgoustakis, K. et al. PLGA-mPEG nanoparticles of cisplatin: in vitro nanoparticle degradation, in vitro drug release and in Vivo drug residence in blood properties. *Journal of Controlled Release* 79, 123-135 (2002).
13. Moghimi, S. M., Hunter, A. C. & Murray, J. C. Nanomedicine: current status and future prospects. *Faseb Journal* 19, 311-330 (2005).
14. Feng, S. S., Mu, L., Win, K. Y. & Huang, G. F. Nanoparticles of biodegradable polymers for clinical administration of paclitaxel. *Current Medicinal Chemistry* 11, 413-424 (2004).
15. Cheng, J. et al. Formulation of functionalized PLGA-PEG nanoparticles for in vivo targeted drug delivery. *Biomaterials* 28, 869-76 (2007).
16. Dechy-Cabaret, O., Martin-Vaca, B. & Bourissou, D. Controlled ring-opening polymerization of lactide and glycolide. *Chemical Reviews* 104, 6147-6176 (2004).
17. Cheng, M., Attygalle, A. B., Lobkovsky, E. B. & Coates, G. W. Single-site catalysts for ring-opening polymerization: Synthesis of heterotactic poly(lactic acid) from rac-lactide. *Journal of the American Chemical Society* 121, 11583-11584 (1999).

18. Pratt, R. C., Lohmeijer, B. G. G., Long, D. A., Waymouth, R. M. & Hedrick, J. L. Triazabicyclodecene: A simple bifunctional organocatalyst for acyl transfer and ring-opening polymerization of cyclic esters. *Journal of the American Chemical Society* 128, 4556-4557 (2006).
19. Chamberlain, B. M. et al. Polymerization of lactide with zinc and magnesium beta-diiminate complexes: Stereocontrol and mechanism. *Journal of the American Chemical Society* 123, 3229-3238 (2001).
20. Nishiyama, N. & Kataoka, K. in Polymer Therapeutics li: Polymers as Drugs, Conjugates and Gene Delivery Systems 67-101 (SPRINGER-VERLAG BERLIN, BERLIN, 2006).
21. Lavasanifar, A., Samuel, J. & Kwon, G. S. Poly(ethylene oxide)-block-poly(L-amino acid) micelles for drug delivery. *Advanced Drug Delivery Reviews* 54, 169-190 (2002).
22. Kwon, G. S. & Kataoka, K. Block-Copolymer Micelles as Long-Circulating Drug Vehicles. *Advanced Drug Delivery Reviews* 16, 295-309 (1995).
23. Farokhzad, O. C. et al. Targeted nanoparticle-aptamer bioconjugates for cancer chemotherapy in vivo. *Proceedings of the National Academy of Sciences of the United States of America* 103, 6315-20 (2006).
24. Cheng, J., Teply, B., Sherifi, I., Langer, R. & Farokhzad, O. Formulation of Functionalized PLGA-PEG Nanoparticles for In Vivo Targeted Drug Delivery. *Biomaterials* 28, 869-876 (2007).

What is claimed is:

1. A method for preparing particles for in vivo delivery of a drug comprising:
(a) providing a drug, the structure of which comprises one or more hydroxyl or thiol groups;
(b) conducting ring-opening polymerization of one or more cyclic monomers, wherein the cyclic monomers are cyclic esters, cyclic carbonates, cyclic phosphate, cyclic silicone, cyclic peptides or amino acid derivatives, or cyclic phosphazane, or a combination thereof, in an anhydrous, water-miscible solvent in the presence of (i) the drug as a polymerization initiator, and (ii) a polymerization catalyst, to form a covalent drug-oligomer or drug-polymer conjugate in the water-miscible solvent, wherein the water-miscible solvent is dimethylformamide (DMF) or tetrahydrofuran (THF), wherein the incorporation efficiency of the drug into the oligomer or polymer is greater than 98%; and
(c) forming particles comprising the drug-oligomer or drug-polymer conjugate by combining the drug-oligomer or drug-polymer conjugate in the water-miscible solvent with water or ether to form the particles, wherein the particles are about 2 nanometers to about 400 micrometers in diameter.

2. The method of claim 1 wherein the particles are nanoparticles having a particle size of about 2 nanometers to about 300 nanometers.

3. The method of claim 1 wherein the particles are nanoparticles having a particle size of about 55 nanometers to 120 nanometers.

4. The method of claim 1 further comprising modifying the surface of the particle.

5. The method of claim 4 wherein the particle surface is modified by coating the particle with a coating layer of a polymer that is the same or different from that of the conjugate.

6. The method of claim 5 wherein the coating layer is surface pegylation and the surface pegylation is provided by forming covalent particle-PEG linkages.

7. The method of claim 5 wherein the coating layer is surface pegylation and the surface pegylation is provided through non-covalent interactions using hydrophobic polymer-b-PEG.

8. The method of claim 4 wherein the surface of the particle formed is modified with a hydrophilic surface modifier, a hydrophobic surface modifier, an amphiphilic polymer, or one or more targeting ligands.

9. The method of claim 8 wherein the surface of the particle formed is modified by covalent or non-covalent attachment to one or more of PEG, an amphiphilic polymer comprising PEG, a peptide, a protein, a saccharide, a carbohydrate, a nucleic acid or a combination thereof.

10. The method of claim 1 wherein the particles have a multilayer structure with different drug concentrations or different types of drugs in different layers.

11. The method of claim 10 wherein the particles have a drug concentration gradient.

12. The method of claim 1 wherein the drug is a hydroxyl-containing small organic molecule.

13. The method of claim 1 wherein the drug is a macromolecule, a peptide, a saccharide or a nucleic acid.

14. The method of claim 1 wherein the drug is abacavir, acetylglycitin, acyclovir, adrenaline, Aeruginosin 298-A, amoxicillin, amphotericin B, Amprenavir (APV), Atazanavir (ATV), bamethane, betaxolol, bithionol, bleomycin, bryostatin 1, camptothecin, captopril, caspofungin, chlorogenic acid/esters, (+)-cylindricine, daidzein, daidzin, darunavir, daunorubicin, didanosine, docetaxel, dopamine, doxorubicin, Emtricitabine (FTC), epirubicin, apothilone A, equol, ethamivan, etoposide, eugenol, fenoterol, fluconazole, (+)-Fostriecin, fulvestrant, Garsubellin A/Hyperforin, genistein, glycitein, hexachlorophene, idarubicin, indinavir, iodoresiniferatoxin, irinotecan, isoprenaline, (+)-Lactacystin, Lamivudine (3TC), Lopinavir (ABT-378), masoprocol, metaraminol, methyldopa, mitoxantrone, alpha-naphthol, natamycin, Nelfinavir (NFV), niclosamide, norepinephrine, (S)-oxybutynin, paclitaxel, pentazocine, phenoxyethanol, phenylephrine, phloroglucinol, podophyllotoxin, polybasic phenols, posaconazole, pyrocatechin, ribavirin, Ritonavir (RTV), salbutamol, salicylanilide, Saquinavir (SQV), Sarcodictyins, SB202190, teniposide, terbutaline, thymol, Tipranavir (TPV), alpha-tocopherol, topotecan, tyrphostin SU1498, valrubicin, vinblastine, vincristine, vindesine, vinorelbine, vinorelbine bitartrate, voriconazole, or Zidovudine (AZT).

15. The method of claim 14 wherein the drug is camptothecin, cyclopamine, docetaxel, doxorubicin, or paclitaxel.

16. The method of claim 1 wherein the cyclic monomers are lactides, glycolides, or a combination thereof.

17. The method of claim 1 wherein the drug-oligomer conjugate comprises 5000 or fewer repeating units of the ring-opened cyclic monomer.

18. The method of claim 1 wherein the molar ratio of cyclic monomer to drug initiator is about 5000/1 to about 2/1.

19. The method of claim 1 wherein the catalyst is an organometallic catalyst of the formula $(BDI)MN(TMS)_2$ where M is Mg or Zn.

20. The method of claim 19 wherein the catalyst is an organometallic catalyst of formula (5):

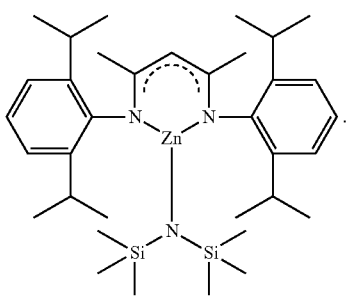

(5)

21. The method of claim 1 wherein the conjugates have a polydispersity of 1.5 or less, as determined by gel permeation chromatography.

22. The method of claim 1 wherein the conjugates have a polydispersity of 1.2 or less, as determined by gel permeation chromatography.

23. The method of claim 1 wherein the drug-oligomer or drug-polymer conjugates of the particles comprise the combination of doxorubicin and cyclopamine, or paclitaxel and cyclopamine, and the combination exerts a synergistic effect after administration to prostate cancer cells.

24. A method for delivery of a drug to an individual in need thereof comprising administering to the individual a pharmaceutical composition comprising nanoparticles prepared by the method of claim 14.

25. A method for preparing particles for in vivo delivery of a drug comprising:

(a) providing a drug, wherein the drug is camptothecin, cyclopamine, docetaxel, doxorubicin, or paclitaxel;
(b) conducting ring-opening polymerization of one or more cyclic monomers, wherein the cyclic monomers are cyclic esters, cyclic carbonates, or a combination thereof, in an anhydrous, water-miscible solvent in the presence of (i) the drug as a polymerization initiator, and (ii) a polymerization catalyst, wherein the polymerization catalyst is an organometallic catalyst of the formula $(BDI)MN(TMS)_2$ where M is Mg or Zn, to form a covalent drug-oligomer or drug-polymer conjugate in the water-miscible solvent, wherein the water-miscible solvent is dimethylformamide (DMF) or tetrahydrofuran (THF), wherein the incorporation efficiency of the drug into the oligimer or polymer is greater than 98%, wherein the drug-oligomer or drug-polymer conjugates have a polydispersity of 1.5 or less, as determined by gel permeation chromatography; and
(c) forming particles comprising the drug-oligomer or drug-polymer conjugate by combining the drug-oligomer or drug-polymer conjugate in the water miscible solvent with water or ether to form the particles, wherein the particles are about 2 nanometers to about 400 micrometers in diameter.

26. The method of claim 25 wherein the drug is paclitaxel, the paclitaxel initiates the ring-opening polymerization exclusively via the hydroxyl group of carbon 2', the cyclic monomers are cyclic esters, the metal M is Zn, and the polydispersity of the conjugates is 1.02 or less, wherein the particles are about 2 nanometers to about 300 nanometers in diameter.

* * * * *